US 11,547,857 B2

United States Patent
Vance et al.

(10) Patent No.: US 11,547,857 B2
(45) Date of Patent: Jan. 10, 2023

(54) METHOD AND DEVICE FOR AVOIDING COMPETITIVE ATRIAL PACING

(71) Applicant: Pacesetter, Inc., Sylmar, CA (US)

(72) Inventors: Jordan Ireland Vance, North Hollywood, CA (US); Joy Catherine Wong, Los Angeles, CA (US); Jennifer Rhude, Carbondale, IL (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 17/395,780

(22) Filed: Aug. 6, 2021

(65) Prior Publication Data
US 2022/0143405 A1    May 12, 2022

Related U.S. Application Data

(60) Provisional application No. 63/112,264, filed on Nov. 11, 2020.

(51) Int. Cl.
*A61N 1/368* (2006.01)
*A61N 1/362* (2006.01)
*A61N 1/365* (2006.01)

(52) U.S. Cl.
CPC ......... *A61N 1/3684* (2013.01); *A61N 1/3622* (2013.01); *A61N 1/3682* (2013.01); *A61N 1/36521* (2013.01); *A61N 1/36585* (2013.01)

(58) Field of Classification Search
CPC .............. A61N 1/3622; A61N 1/36521; A61N 1/36585; A61N 1/3682; A61N 1/3684
See application file for complete search history.

(56) References Cited

U.S. PATENT DOCUMENTS

| | | | | |
|---|---|---|---|---|
| 2002/0147472 | A1* | 10/2002 | Seim | A61N 1/3621 607/14 |
| 2008/0036777 | A1* | 2/2008 | Fossum | G06T 17/05 345/543 |
| 2017/0232262 | A1* | 8/2017 | Shilling | A61N 1/3684 607/28 |

* cited by examiner

*Primary Examiner* — Brian T Gedeon
(74) *Attorney, Agent, or Firm* — The Small Patent Law Group LLC; Dean D. Small

(57) ABSTRACT

Methods and devices herein are provided for managing atrial (A) pacing in connection with premature atrial contracts (PAC). The methods and devices obtain an atrial pace-on-PAC (APAC) interval and cardiac activity (CA) signals. The methods and devices are configured to: i) during a first cardiac beat; following a ventricular paced (VP) or ventricular sensed (VS) event, activate a timer for a post ventricular-atrial refractory period (PVARP) interval; and determine whether a first atrial refractory (AR) event occurs during the PVARP interval; ii) during a second cardiac beat; in response to the detecting that the first AR event occurred, initiate an APAC interval; during the APAC interval for the second cardiac beat, determine whether a second AR event occurs; and update a count of APAC events when the second AR event occurs; and iii) repeat i) and ii) for multiple cardiac beats, to track the count of APAC events.

20 Claims, 14 Drawing Sheets

- PVC results in a retrograde P wave
- This P wave falls into PVARP
- Atrial pacing impulse is delivered into refractory tissue
- Since AP does not capture, no AV conduction occurs, ventricular pacing impulse is delivered
- Retrograde P wave falls into PVARP and the cycle continues FIG. 6
Continued

METHOD AND DEVICE FOR AVOIDING COMPETITIVE ATRIAL PACING

CROSS-REFERENCE TO RELATED APPLICATIONS

This application claims priority benefit to U.S. Provisional Application No. 63/112,264, which was filed on 11 Nov. 2020, and the entire disclosure of which is incorporated herein by reference in its entirety.

BACKGROUND

Embodiments of the present disclosure generally relate to methods and devices for managing therapy to avoid competitive atrial pacing.

Today, various types of implantable medical devices (IMDs) have been implemented to provide therapies in connection with various arrhythmias, such as bradycardia, tachycardia and the like. A relatively large portion of existing IMDs deliver atrial and ventricular pacing therapies in a dual chamber configuration.

However, a problem may arise when the patient's physiologic behavior negatively interacts with the dual chamber operation of the IMD in a manner that results in competitive atrial pacing, which may result in an arrhythmia. Competitive atrial pacing is the phenomenon where an atrial pacing output occurs soon after a sensed atrial event (e.g., a premature atrial contraction or PAC) that has occurred during the atrial refractory period. Competitive atrial pacing may arise as a consequence of the IMD attempting to modulate the pacing rate and heart rate response to patient activity and physiologic conditions. Competitive atrial pacing may result in adverse outcomes such as Repetitive Non-reentrant Ventriculoatrial Synchrony (RNRVAS), induction of an atrial arrhythmia by pacing during the atrial vulnerable period, and induction of a ventricular arrhythmia via ventricular pacing soon after atrial pacing due to pseudo-psuedo-fusion (atrial pacing simultaneous to an intrinsic ventricular event, resulting in an unintentional blanked ventricular intrinsic event).

Conventional IMDs have attempted to resolve competitive atrial pacing, such as utilizing an algorithm referred to as a non-competitive atrial pacing (NCAP) algorithm, which allows the device to detect a refractory sensed atrial event and extend the IMD's atrial refractory period for a programmed number of milliseconds (200-400 ms in 50 ms intervals, nominally 300 ms). This delays the atrial paced event and allows the patient's physiologic atrial refractory period to end, reducing the likelihood of atrial pacing during the atrial vulnerable period. When an atrial pacing stimulus is delayed by the NCAP algorithm, the IMD attempts to maintain a stable ventricular rate by shortening the following atrial-ventricular (AV) interval, with a minimum AV interval of 30 ms. There are no diagnostics associated with NCAP operation.

When an atrial event is sensed during a post ventricular atrial refractory period (PVARP), the event introduces the potential for three adverse outcomes. For example, repetitive non-reentrant ventricular-atrial synchrony (RNRVAS) may occur, in which an atrial arrhythmia is induced by pacing during the atrial vulnerable period and a ventricular arrhythmia may be induced by pacing soon after an unintentionally blanked ventricular intrinsic event. RNRVAS represents a pacemaker mediated arrhythmia. A retrograde arrhythmia event that occurs during PVARP is ignored and subsequent atrial pacing occurs, however there is functional loss of capture. Subsequently, the device tracks the atrial paced event and utilizes the atrial paced event in connection with determining a timing for a ventricular paced event, which then retrogradely conducts to the atrium. The pattern is then repeated.

The foregoing phenomenon results in loss of AV synchrony in exchange for VA synchrony which reduces hemodynamic stability by removing the contribution of the atrial kick to ventricular filling. The repetitive nature of the foregoing pacemaker mediated arrhythmia also increases the possibility that instead of failing to capture, the subsequent paced event occurs during a vulnerable window of the atrial refractory period and induces an atrial arrhythmia. Further, atrial arrhythmias such as atrial fibrillation are an increasingly prevalent cardiac pathology that among other things, reduces cardiac output.

A need remains for a solution that reduces a T/AF occurrence or burden to improve patient quality of life in clinical outcome.

Another potential adverse outcome is the induction of a ventricular arrhythmia, albeit less likely. The atrial event that occurs during the PVARP interval may subsequently conduct of the ventricle and it is possible that a competing atrial paced pulse may cause the intrinsic event to be hidden by the ventricular blanking period that follows atrial pacing. If an intrinsic VS is blanked by an AP event, the device may track the AP event followed by AVP event which introduces the possibility of inducing a ventricular arrhythmia if that the PA event is delivered during an intrinsic T wave. However, conventional approaches to addressing competitive atrial pacing still experience certain limitations.

Further, one solution that has been attempted for non-competitive atrial pacing is to prevent triggering an atrial tachycardia by delaying a scheduled atrial paced event from occurring within an atrium's relative refractory period. In the foregoing proposed solution, when an intrinsic atrial event occurs during the PVARP, the PVARP is extended by a fixed amount (e.g., 300 ms). In addition, the ventricular pacing interval is maintained on a sliding scale that seeks to maintain a V-V interval, which causes the AV delay to be adjusted between a maximum AV delay down to 30 ms. Adjusting the AV delay in this manner to maintain a target V-V interval can create variability and unpredictability. For example, when the AV interval falls below 80 ms, the system may not achieve the full benefit of the "atrial kick" at the end of the atrial contraction.

A need remains for methods and devices that provide an improved approach for addressing competitive atrial pacing.

SUMMARY

In accordance with an embodiment, methods and systems are provided that addresses atrial competitive pacing. Methods and systems herein are configured to ensure that a minimum interval occurs between a premature atrial contraction (occurring during an atrial refractory period) and a subsequent atrial paced event. The methods and systems initiates an IMD alert period for a programmed number of milliseconds (200-400 ms in 10 ms intervals, nominal 330 ms) in the IMD after the IMD detects a refractory sensed atrial event. This allows for the IMD to detect and respond to intrinsic atrial and ventricular events while providing a method to delay the atrial paced event. If an intrinsic atrial or ventricular event occurs during the IMD alert period, the algorithm is cancelled, allowing the patient's native rhythm to continue. If no intrinsic atrial or ventricular event is detected during the IMD alert period, the delayed atrial paced event would occur after having allowed the patient's physiologic atrial refractory period to recover during the programmed IMD alert period. In the situation where a delayed atrial pacing stimulus is delivered by the IMD, the following atrial-ventricular (AV) interval is set to a fixed value of 100 ms to maintain a reasonable delay for AV synchrony while minimizing the ventricular rate change. Additionally, this algorithm provides diagnostics related to consecutive triggering of the algorithm response, including a programmable stored electrogram (SEGM) storage trigger.

In accordance with new and unique aspects herein, the methods and systems further add a response to interactions with another algorithm, Ventricular Intrinsic Preference (VIP), which extends AV delays in order to encourage intrinsic conduction. The AV delay extension can also encourage the patient's native rhythm behavior. In cases where VIP has extended the AV delay resulting in an atrial refractory event following a paced ventricular event, embodiments herein respond as described below and additionally cancel the AV delay extension to prevent repetitive occurrences.

In accordance with new and unique aspects herein, an implantable medical device (IMD) is provided for managing atrial (A) pacing in connection with premature atrial contracts (PAC). The IMD comprises memory configured to store program instructions and an atrial pace-on-PAC (APAC) interval; a sensing channel configured to sense cardiac activity (CA) signals; and one or more processors that, when executing the program instructions in a dual chamber mode, are configured to: i) during a first cardiac beat; following a ventricular paced (VP) or ventricular sensed (VS) event, activate a timer for a post ventricular-atrial refractory period (PVARP) interval; and determine whether a first atrial refractory (AR) event occurs during the PVARP interval; ii) during a second cardiac beat; in response to the detecting that the first AR event occurred, initiate an APAC interval; during the APAC interval for the second cardiac beat, determine whether a second AR event occurs; and update a count of APAC events when the second AR event occurs; and iii) repeat i) and ii) for multiple cardiac beats, to track the count of APAC events.

Additionally or alternatively, one or more processors are further configured to determine when the count of APAC events exceeds a threshold and in response thereto, transmitting APAC related diagnostics to an external device. Additionally or alternatively, the APAC related diagnostics include IEGM signals for the multiple beats that included the APAC events. Additionally or alternatively, the one or more processors are further configured to obtain an atrial alert period, compare the atrial alert period to the APAC interval and manage the initiation of the APAC interval based on the comparing. Additionally or alternatively, when the atrial alert period is less than or equal to the APAC interval, the one or more processors are further configured to perform the initiate, determine and update operations in connection with the second cardiac beat. Additionally or alternatively, when the atrial alert period is greater than the APAC interval, the one or more processors are further configured to reset the count of the APAC events and omit the initiate, determine and update operations in connection with the second cardiac beat. Additionally or alternatively, the IMD further comprises a transmitter configured to communicate with a second IMD to obtain the CA signals, perform the i) and ii) operations and track the count the APAC events. Additionally or alternatively, the APAC interval has a duration set to achieve a desired time delay between the AR event and a next atrial paced event, the duration of the APAC interval greater than a right atrium functional refractory period such that the next atrial paced event captures the atrium. Additionally or alternatively, the APAC interval runs concurrently with at least a portion of the PVARP interval, and the PVARP interval will time out before the APAC interval. Additionally or alternatively, the CA signals represent at least one of electrical CA signals, heart sound CA signals or impedance CA signals.

Additionally or alternatively, the one or more processors are further configured to start a programmed APAC AV delay that represents an AV delay to be utilized following an occurrence of an AS or AP event in connection with the APAC interval. Additionally or alternatively, the APAC AV delay is configured to limit or minimize a ventricular rate change, while maintaining a desired AV synchrony and while limiting or minimizing a possibility of induction by reducing a possibility of pacing during a vulnerable period. Additionally or alternatively, the one or more processors are further configured to discontinue an extension of an AV interval when the APAC AV delay is started.

In accordance with new and unique aspects herein, a method is provided for managing atrial (A) pacing in connection with premature atrial contracts (PAC). The method comprises: obtaining an atrial pace-on-PAC (APAC) interval; obtaining cardiac activity (CA) signals; and under control of one or more processors within one or more implantable medical device (IMD) operating in a dual chamber mode, i) during a first cardiac beat; following a ventricular paced (VP) or ventricular sensed (VS) event, activating a timer for a post ventricular-atrial refractory period (PVARP) interval; and determining whether a first atrial refractory (AR) event occurs during the PVARP interval; ii) during a second cardiac beat; in response to the detecting that the first AR event occurred, initiating an APAC interval; during the APAC interval for the second cardiac beat, determining whether a second AR event occurs; and updating a count of APAC events when the second AR event occurs; and iii) repeating i) and ii) for multiple cardiac beats, to track the count of APAC events.

Additionally or alternatively, the method further determines when the count of APAC events exceeds a threshold and in response thereto, transmitting APAC related diagnostics to an external device. Additionally or alternatively, the APAC related diagnostics include IEGM signals for the multiple beats that included the APAC events. Additionally or alternatively, the method further comprises obtaining an atrial alert period, comparing the atrial alert period to the APAC interval and managing the initiating of the APAC interval based on the comparing. Additionally or alternatively, when the atrial alert period is less than or equal to the APAC interval, performing the initiating, determining and updating in connection with the second cardiac beat. Additionally or alternatively, when the atrial alert period is greater than the APAC interval, resetting the count of the APAC events and omitting the initiating, determining and updating in connection with the second cardiac beat. Additionally or alternatively, the APAC interval at least partially overlaps the PVARP interval. Additionally or alternatively, the APAC interval has a duration set to achieve a desired time delay between the AR event and a next atrial paced event, the duration of the APAC interval greater than a right atrium functional refractory period such that the next atrial paced event captures the atrium. Additionally or alternatively, the APAC interval runs concurrently with at least a portion of the PVARP interval, and the PVARP interval will time out before the APAC interval. Additionally or alternatively, the CA signals represent at least one of electrical CA signals, heart sound CA signals or impedance CA signals.

DETAILED DESCRIPTION

Figure 1:
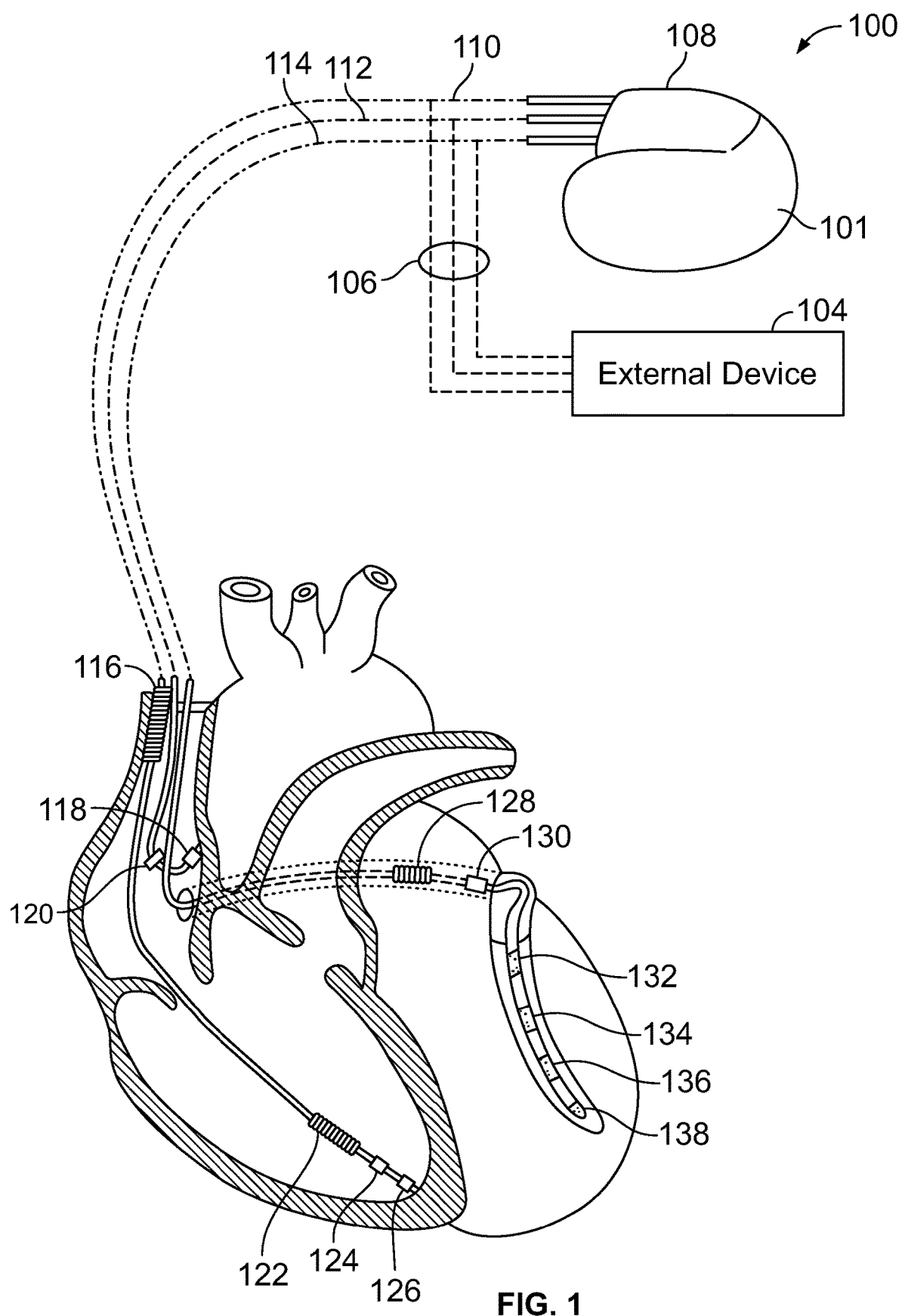
FIG. 1 illustrates an IMD 100 and external device 104 coupled to a heart in a patient and implemented in accordance with one embodiment.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The term "alert period" shall mean a window or interval that is initiated in response to a paced or sensed event in a chamber of interest, during which the IMD monitors sensed CA signals over one or more channels in search of desired intrinsic cardiac activity from the same chamber of interest. When the desired physiologic activity is detected during the "alert period" or window, the IMD suspends pacing in the chamber of interest for the next cardiac cycle. For example, an atrial alert period represents a window that is initiated in response to a paced or sensed atrial event and, during the window, the IMD monitors sensed atrial CA signals in search of a next successive desired intrinsic atrial event. When the desired intrinsic atrial activity is detected during the atrial alert period, the IMD suspends pacing in the atrium for the next cardiac cycle.

The term "refractory period" shall mean a window or interval that is initiated in response to a paced or sensed event in a chamber of interest, during which the IMD monitors sensed CA signals over one or more channels in search of undesired non-physiologic intrinsic cardiac activity from the same or a different chamber. The undesired non-physiologic activity should not occur as the tissue in the corresponding chamber should be in a refractory state and should not initiate an intrinsic event. For example, a post ventricular atrial refractory period represents a window that is initiated in response to a paced or sensed ventricular event and, during the window, the IMD monitors sensed atrial CA signals in search of undesired non-physiologic intrinsic atrial event. When the undesired intrinsic atrial activity is detected during the PVARP, the IMD takes various corrective actions.

The terms "atrial pace-on-PAC interval" and "APAC interval" shall mean a programmed atrial to atrial (A-A) interval between an intrinsic or paced atrial event and a next successive atrial paced event in the absence of an intervening intrinsic atrial event. For example, the APAC interval may be programmed to between 300 ms and 400 ms, or more preferably between 300 ms and 330 ms. If no other factors or timers/intervals intervene, once an intrinsic atrial event or paced atrial event is sensed, the next successive paced atrial event will be delivered if an intrinsic atrial event does not occur within the APAC interval.

The terms "atrial refractory event" and "AR event" shall mean an intrinsic atrial event or AS event that occurs during a period in which the atrial tissue is in refractory state.

The terms "cardiac activity signal", "cardiac activity signals", "CA signal" and "CA signals" (collectively "CA signals") are used interchangeably throughout to refer to measured signals indicative of cardiac activity by a region or chamber of interest. For example, the CA signals may be indicative of impedance, electrical or mechanical activity by one or more chambers (e.g, left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes EGM signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The terms "dual chamber mode" and "DDD mode" shall mean a combination of pacing and sensing capabilities in at least one atrial and at least one ventricle of the heart, such as pacing/sensing in the RA and pacing/sensing in the RV. The term "DDDR mode" shall mean one or more IMDs operating in the DDD mode and that include rate responsive functionality.

The term "leadless" shall mean an absence of transvenous and/or subcutaneous electrically, conductive leads that would otherwise traverse vessels or other anatomy inside or outside of an intra-cardiac space.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "refractory period" and "refractory interval" shall mean an interval following a paced or sensed event in a chamber of interest, during which the IMD is not reset and during which the IMD does not sense and does not respond to intrinsic events. For example, an atrial refractory period is triggered after an atrial sensed or paced event. During the atrial refractory period sensing is disabled over and atrial channel and events occurring in the atrial refractory period are not counted as intrinsic events.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

FIG. 1 illustrates an IMD 100 and external device 104 coupled to a heart in a patient and implemented in accordance with one embodiment. The external device 104 may be a programmer, an external defibrillator, a workstation, a portable computer, a personal digital assistant, a cell phone, a bedside monitor and the like. The IMD may represent a cardiac monitoring device, pacemaker, cardioverter, cardiac rhythm management device, defibrillator, neurostimulator, leadless monitoring device, leadless pacemaker and the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-Z38 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and then transmitted wirelessly to the external device 104. Hence, the external device 104 receives the IEGM cardiac signals through telemetry circuit inputs. The physician or another user controls operation of the external device 104 through a user interface.

Figure 2:
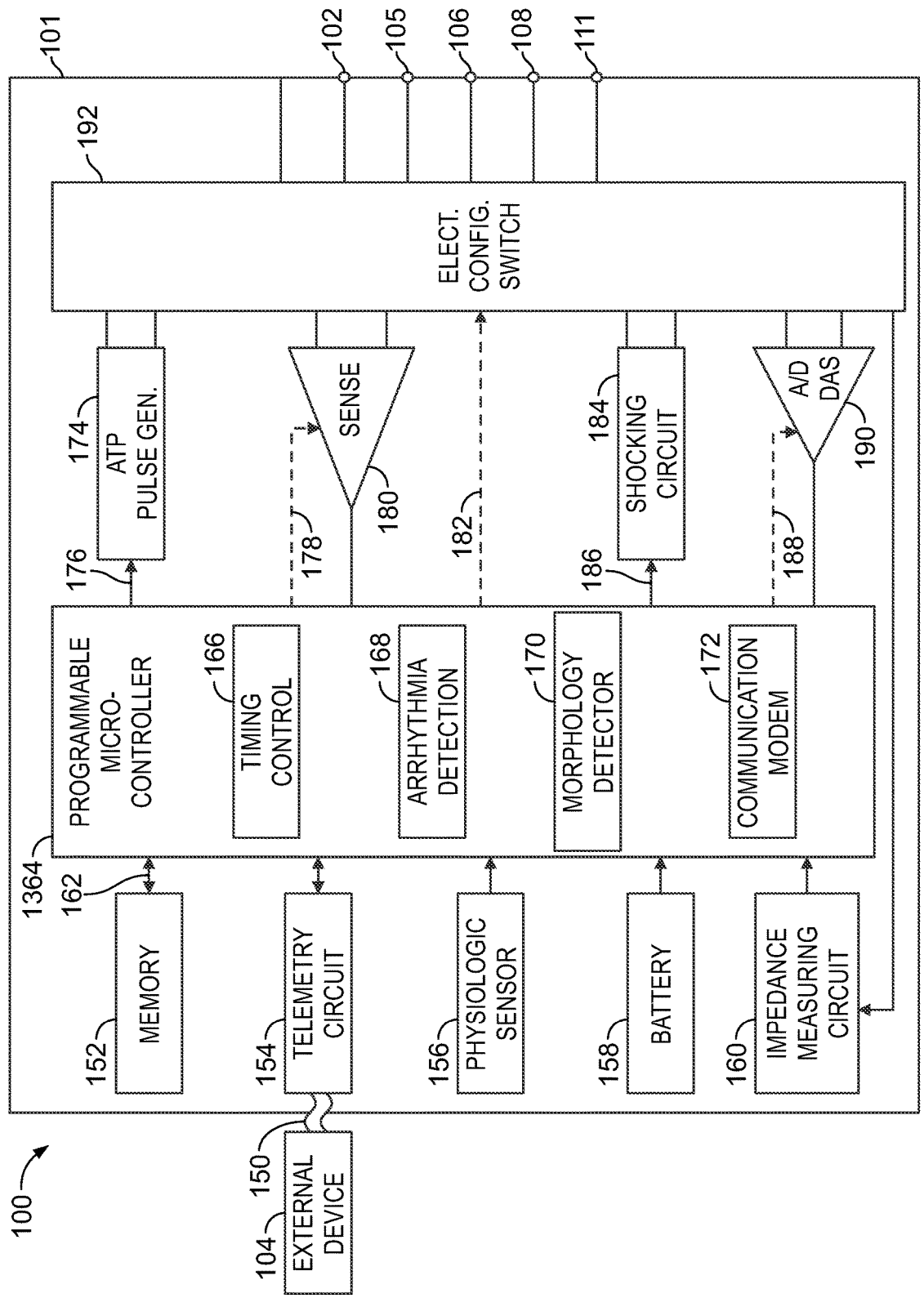
FIG. 2 illustrates a simplified block diagram of a device formed in accordance with embodiments herein.

FIG. 2 illustrates a block diagram of the IMD 100 formed in accordance with embodiments herein. The housing 101 (which is often referred to as the "can", "case", "encasing", or "case electrode") may be programmably selected to act as the return electrode for certain stimulus modes. Housing 101 further includes a connector (not shown) with a plurality of terminals 102, 105, 106, 108, and 111. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 111 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. Microcontroller 164 includes a microprocessor (or equivalent control circuitry), RAM and/or ROM memory, logic and timing circuitry, state machine circuitry, and I/O circuitry.

IMD 100 further includes a first chamber pulse generator 174 that generates stimulation pulses for delivery by one or more electrodes coupled thereto. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164. In the example of FIG. 2, a single pulse generator 174 is illustrated. Optionally, the IMD 100 may include multiple pulse generators, similar to pulse generator 174, where each pulse generator is coupled to one or more electrodes and controlled by the microcontroller 164 to deliver select stimulus pulse(s) to the corresponding one or more electrodes.

Microcontroller 164 is illustrated to include timing control circuitry 166 to control the timing of the stimulation pulses (e.g., pacing rate, atrio-ventricular (AV) delay, atrial interconduction (A-A) delay, or ventricular interconduction (V-V) delay, etc.). The timing control circuitry 166 may also be used for the timing of refractory periods, blanking intervals, noise detection windows, evoked response windows, alert periods, marker channel timing, and so on. Microcontroller 164 also has an arrhythmia detector 168 for detecting arrhythmia conditions and a morphology detector 170 to review and analyze one or more features of the morphology of cardiac signals. Although not shown, the microcontroller 164 may further include other dedicated circuitry and/or firmware/software components that assist in monitoring various conditions of the patient's heart and managing pacing therapies. The timing control circuitry 166 may be configured to implement the processes described herein including adjustment of the alert period.

The IMD 100 is further equipped with a communication modem (modulator/demodulator) 172 to enable wireless communication with other devices, implanted devices and/or external devices. In one implementation, the communication modem 172 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient. The communication modem 172 may be implemented in hardware as part of the microcontroller 164, or as software/firmware instructions programmed into and executed by the microcontroller 164. Alternatively, the modem 172 may reside separately from the microcontroller as a standalone component.

The IMD 100 includes sensing circuitry 180 selectively coupled to one or more electrodes that perform sensing operations, through the switch 192 to detect the presence of cardiac activity in the right chambers of the heart. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 192 determines the sensing polarity of the cardiac signal by selectively closing the appropriate switches. In this way, the clinician may program the sensing polarity independent of the stimulation polarity. The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuit, similar to sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or in a bipolar sensing configuration. The IMD 100 further includes an analog-to-digital (ND) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The operating parameters of the IMD 100 may be non-invasively programmed into the memory 152 through a telemetry circuit 154 in telemetric communication via communication link 150 with the external device 104. The telemetry circuit 154 allows intracardiac electrograms and status information relating to the operation of the IMD 100 (as contained in the microcontroller 164 or memory 152) to be sent to the external device 104 through the established communication link 150.

The IMD 100 can further include magnet detection circuitry (not shown), coupled to the microcontroller 164, to detect when a magnet is placed over the unit. A magnet may be used by a clinician to perform various test functions of the unit 100 and/or to signal the microcontroller 164 that the external programmer is in place to receive or transmit data to the microcontroller 164 through the telemetry circuits 154.

The IMD 100 can further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. The microcontroller 164 responds by adjusting the various pacing parameters (such as rate, AV Delay, V-V Delay, etc.) at which the atrial and ventricular pacing pulses are administered. While shown as being included within the unit 100, the physiologic sensor(s) 156 may be external to the unit 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the unit 100 employs lithium/silver vanadium oxide batteries. The IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 164 further controls a shocking circuit 184 by way of a control signal 186. The shocking circuit 180 generates shocking pulses of low (e.g., up to 0.5 joules), moderate (e.g., 0.5-10 joules), or high energy (e.g., 111 to 40 joules), as controlled by the microcontroller 164. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Figure 3A:
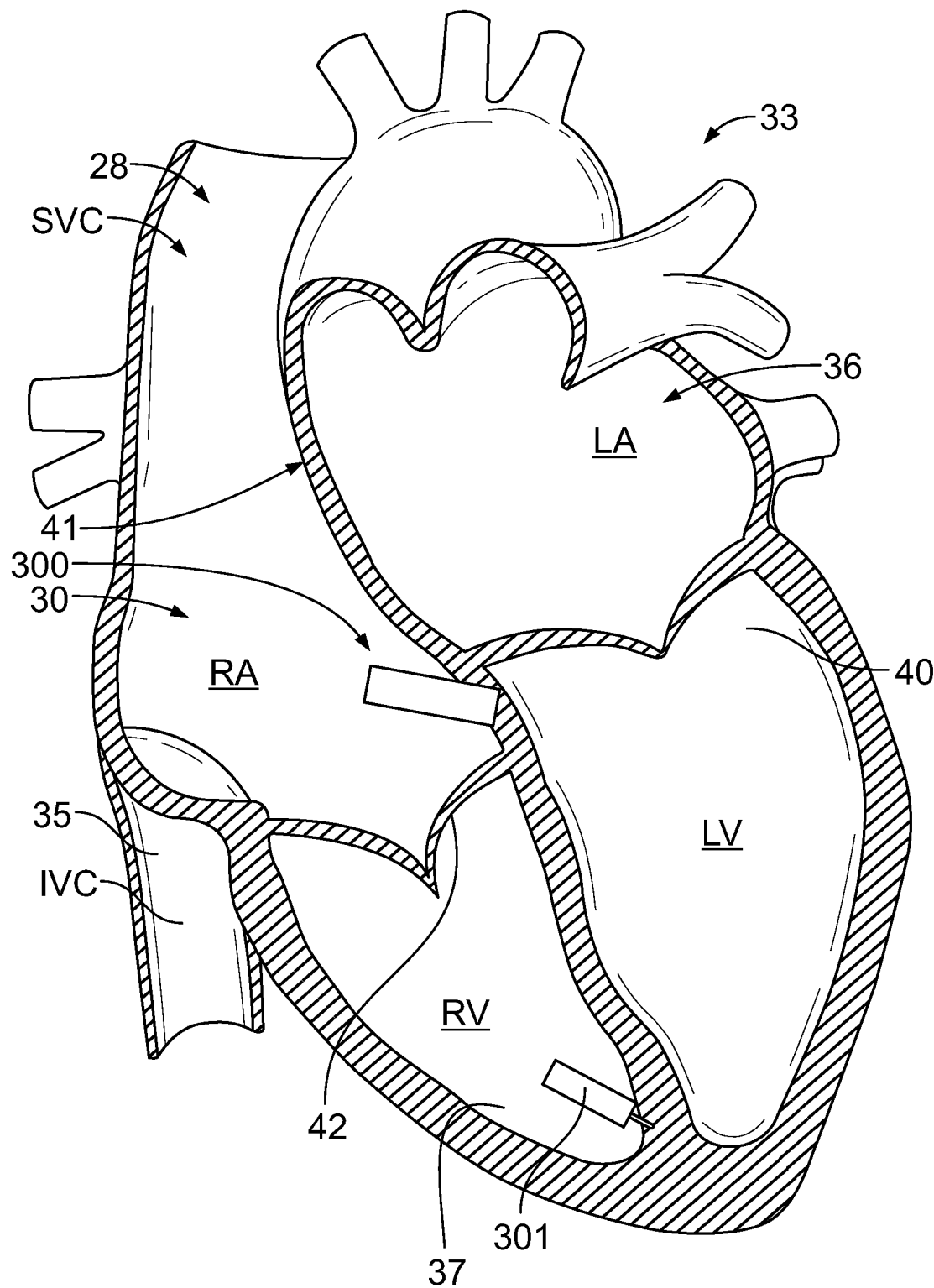
FIG. 3A illustrates leadless IMDs implanted in different chambers of the heart in accordance with embodiments herein.

FIG. 3A illustrates leadless IMD 300 and IMD 301 implanted in different chambers of the heart in accordance with embodiments herein. The leadless IMD 300 has been placed through the superior vena cava 28 into the right atrium 30 of the heart 33, while the IMD 301 has been implanted proximate the apex of the RV. FIG. 3A also shows the inferior vena cava 35, the left atrium 36, the right ventricle 37, the left ventricle 40, the atrial septum 41 that divides the two atria 30, 36, the ventricular vestibule VV, the right atrial appendage (RAA), and the tricuspid valve 42 between the right atrium 30 and right ventricle 37. The reader will appreciate that the view of FIG. 3A is simplified and somewhat schematic, but that nevertheless FIG. 3A and the other views included herein will suffice to illustrate adequately the placement and operation of embodiments of the present invention. The term "septum" shall be used throughout to generally refer to any portion of the heart separating two chambers (e.g., RA to LA, RV to LV). The LIMDs 300, 301 may represent pacemakers that cooperate to provide a DDD mode or a DDDR-mode functionality, a cardiac resynchronization device, a cardioverter, a defibrillator and the like. When in DDD or DDDR-mode, the LIMDs 300, 301 may sense in two chambers, pace in two chambers and inhibit pacing in either chamber based on intrinsic events sensed in that chamber or in the other chamber. The LIMDs 300, 301 each comprises a housing configured to be implanted entirely within a single local chamber of the heart.

Optionally, a single LIMD 300 may be utilized and configured to implement DDD or DDDR mode functionality. For example, the single LIMD 300 may be configured to perform far field sensing to monitor ventricular activity and based thereon, provide pacing pulses in the RA and/or proximate to the His bundle.

Optionally, the LIMDs 300 and 301 may both be located in the RA, where the LIMD 300 is implanted at a position to stimulate the right atrium, while the LIMD 301 is implanted at a location proximate to the His bundle and managed to deliver His bundle pacing in a manner that stimulates the RV.

For convenience, hereafter the chamber in which the LIMD 300 is implanted shall be referred to as the "local" chamber. The local chamber includes a local chamber wall that is physiologically response to local activation events originating in the local chamber. The local chamber is at least partially surrounded by local wall tissue that forms or constitutes at least part of a conduction network for the associated chamber. For example, during normal operation, the wall tissue of the right atrium contracts in response to an intrinsic local activation event that originates at the sinoatrial (SA) node and in response to conduction that propagates along the atrial wall tissue. For example, tissue of the right atrium chamber wall in a healthy heart follows a conduction pattern, through depolarization, that originates at the SA node and moves downward about the right atrium until reaching the atria ventricular (AV) node. The conduction pattern moves along the chamber wall as the right atrium wall contracts.

The term "adjacent" chamber shall refer to any chamber separated from the local chamber by tissue (e.g., the RV, LV and LA are adjacent chambers to the RA; the RA and LV are adjacent chambers to the LA; the RA and RV are adjacent to one another; the RV and LV are adjacent to one another, and the LV and LA are adjacent to one another).

The local chamber (e.g., the right atrium) has various tissue of interest, such as a septum, that separate the local chamber from the adjacent chambers (e.g., right ventricle, left atrium, left ventricle). In certain portions or segments of the septum, segments of the septum, behave in physiologically different manners. For example, in certain segments of the septum for the right atrium, even during normal healthy operation, the septum wall tissue does not propagate the conduction in the same manner or pattern as in a majority of the wall tissue of the right atrium wall. For example, septum wall tissue in the right atrium, referred to as the ventricular vestibule tissue, does not behave physiologically in the same manner as the non-septum atrial wall tissue. Instead, the right ventricular vestibule tissue is physiologically coupled to the wall tissue in the right ventricle and in accordance therewith exhibits a conduction pattern that follows the conduction pattern of the right ventricular wall tissue. The right ventricular vestibule tissue is one example of a septum segment that partially separates a local chamber (e.g., the right atrium) from an adjacent chamber (e.g., right ventricle), yet is physiologically coupled to conduction in the adjacent chamber (e.g., right ventricle).

In the example of FIG. 3A, the LIMD 300 is implanted in an area near different regions of tissue that follow the conductive pattern of different chambers of the heart. Optionally, the LIMD 300 may be implanted such that at least one electrode on the base of the LIMD 300 engages tissue that is part of the conductive network of the one chamber, while at least one other electrode projects from the base into tissue that is part of the conductive network of another chamber. For example, when the LIMD 300 may be implanted within or near the triangle of Koch in an area adjacent the ventricular vestibule. The conductive network of the tissue in the ventricular vestibule follows the conductive pattern of the right ventricle. Therefore, the LIMD 300 may be implanted near the edge of the triangle of Koch such that one or more proximal electrodes, extending from the LIMD 300, are electrically coupled to the conductive network of the right atrium, while one or more other distal electrodes, extend diagonally to become electrically coupled to the conductive network of the right ventricle (e.g., the ventricular vestibule). Optionally, the LIMD 300 may be positioned with the base located against the RA wall above the mitral valve, but with a distal electrode that projects into the septum to ventricular tissue of the right or left ventricle.

Figure 3B:
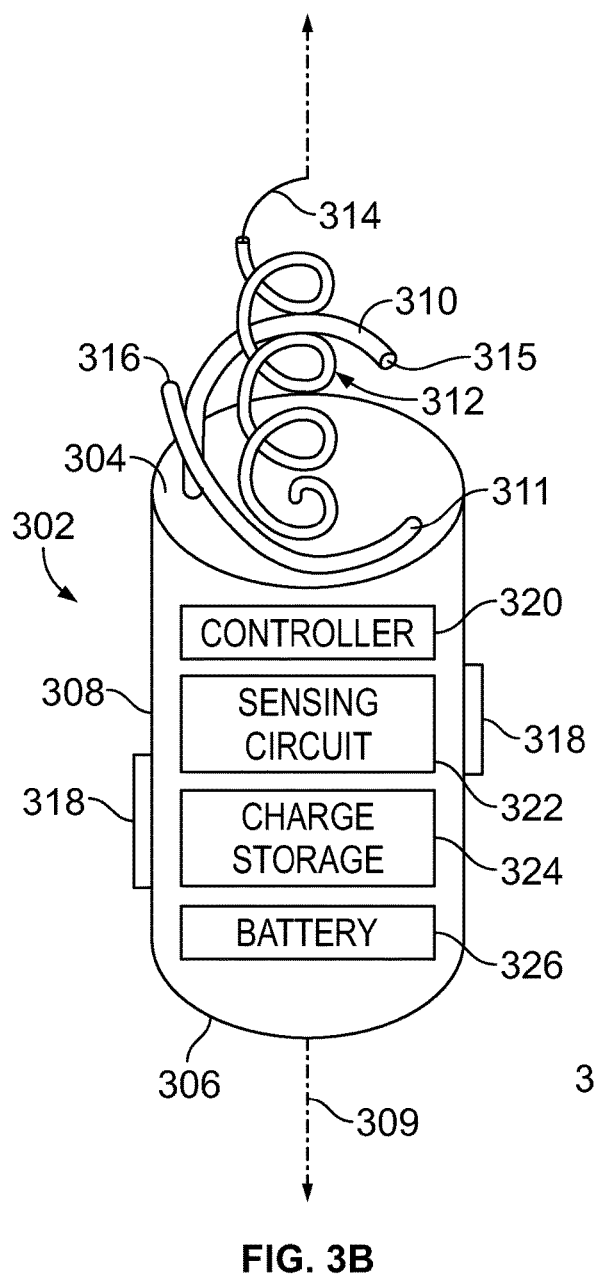
FIG. 3B illustrates a side perspective view of the LIMDs of FIG. 3A oriented with the base facing upward to illustrate electrodes in more detail.
Figure 4:
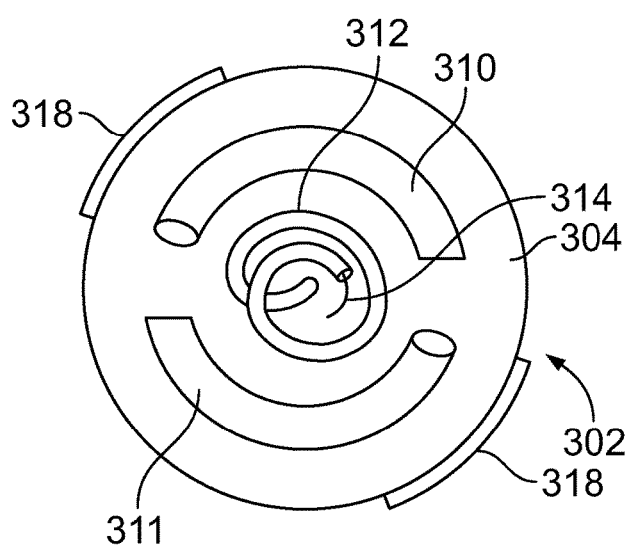
FIG. 4 illustrates a bottom plan view of the LIMDs.

FIGS. 3B and 3C illustrate the LIMDs 300, 301 in more detail. FIG. 3B illustrates a side perspective view of the LIMDs 300, 301 of FIG. 3A oriented with the base 304 facing upward to illustrate electrodes 310-312 in more detail. FIG. 3C illustrates a bottom plan view of the LIMD 300, 301. The LIMD 300 comprises a housing 302 having a proximal base 304, a distal top end 306, and an intermediate shell 308 extending between the proximal base 304 and the distal top end 306. The shell 308 is elongated and tubular in shape and extends along a longitudinal axis 309.

The base 304 includes one or more electrodes 310-312 securely affixed thereto and projected outward. For example, the outer electrodes 310, 311 may be formed as large semi-circular spikes or large gauge wires that wrap only partially about the inner electrode 312. The electrodes 310, 311 may be located on opposite sides of, and wound in a common direction with, the inner electrode 312. The first or outer electrodes 310, 311 are provided directly on the housing 302 of the LIMD 300 at a first position, namely at or proximate a periphery of the base 304 of the housing. The outer electrodes 310, 311 are positioned near the periphery of the base 304 such that, when the LIMD 300 is implanted in the local chamber (e.g., right atrium), the outer electrodes 310, 311 engage the local chamber wall tissue at tissue of interest for a local activation site that is near the surface of the wall tissue, and that is within the conduction network of the local chamber. The outer electrodes 310, 311 are physically separated or bifurcated from one another and have separate distal outer tips 315, 316. The outer electrodes 310, 311 are electrically joined to one another (i.e., common), but are electrically separated from the inner electrode 312.

The second or inner electrode 312 is also provided directly on the housing 302 of the LIMD 300 at a second position, namely at or proximate to a central portion of the base 304 of the housing. The inner electrode 312 is positioned near the center of the base 304 and is elongated such that, when the LIMD 300 is implanted in the local chamber, the inner electrode 312 extends a majority of the way through the wall tissue (e.g., septum) until reaching tissue of interest near the adjacent chamber wall. The inner electrode 312 is inserted to a depth such that a distal tip thereof is located at tissue of interest for an activation site that is physiologically coupled to wall tissue of the adjacent chamber (e.g., right ventricle). For example, the inner electrode 312 may extend until the distal tip extends at least partially through a septum to a position proximate to a distal wall tissue within the conduction network of the adjacent chamber. Optionally, the inner electrode 312 may be inserted at a desired angle until the distal end enters the ventricular vestibule. By located the distal tip of the inner electrode 312 at an adjacent chamber activation site, the inner electrode 312 initiates contraction at a distal activation site within the conduction network of the adjacent chamber without physically locating the LIMD 300 in the adjacent chamber. The inner and outer electrodes 310-312 may be formed as multiple cathode electrodes that are actively fixated to the myocardium. The outer cathode electrodes 310, 311 may be configured as screws with a large pitch (e.g., length between adjacent turns), large diameter and may have a length that is relatively short, while the inner electrode 312 is configured as a screw with a common or smaller pitch, small diameter and longer length. The screw shape of the outer electrodes 310, 311 is used to firmly adhere them to the cardiac tissue. The outer electrodes 310, 311 may have very little or no insulation material thereon to facilitate a good electrical connection to local wall tissue along the majority or the entire length of the outer electrodes 310, 311 for delivering stimulus pulses and sensing electrical activity in the local chamber where the LIMD 300 is located.

The inner electrode 312 is shaped in a helix or screw and is longer (e.g., extends a greater distance from the base) than the outer electrodes 310, 311. The inner electrode 312 is fashioned to an appropriate length that permits it to drill a predetermined distance into, or entirely through, the septum at the desired location. For example, the inner electrode 312 may be provided with a desired length sufficient to extend through, or to a desired distance into, a septum region separating two chambers of the heart. For example, the outer electrodes 310, 311 may contact atrial wall tissue within the triangle of Koch, while the inner electrode 312 extends diagonally along the septum into the ventricular vestibule.

The inner electrode 312 may be formed as a single conductive wire or a bundle of conductive wires, where a proximal portion of the wire is covered with insulation, while the distal tip 314 is covered with insulation and is exposed. By covering the proximal portion of the electrode 312 with insulation, this limits electrical conduction of the conductive wire to tissue surrounding the distal tip 314. When implanted, the distal tip 314 of the electrode is located far below the surface tissue of the chamber wall in which the LIMD 300 is located. As a consequence, the distal tip 314 of the inner electrode 312 directly engages or is located proximate to the surface tissue of an adjacent chamber wall. Hence, the distal tip will 314 senses electrical activity from the conductive network of the adjacent chamber that is representative of physiologic behavior (e.g., conduction pattern) of the adjacent chamber. Also, when delivering stimulus pulses, the distal tip 314 will deliver the pulses into the conductive network of the adjacent chamber wall.

The combination of the inner and outer screw type electrodes 310-312 also imparts extra mechanical stability to the LIMD 300, preventing unwanted torque and shear effects as the heart wall moves during contraction. Otherwise, such effects would otherwise predispose the LIMD 300 to dislodgement. Extraction could simply entail a combination of unscrewing of the two cathodes in conjunction with a slight tugging force directed away from the myocardial wall. Optionally, a single anode electrode or multiple anode electrodes 318 may be provided. The anode electrode(s) 318 may be located along one or more sides of the shell 308, and/or on the top end 306 of the LIMD 300.

The LIMD 300 includes a charge storage unit 324 and sensing circuit 322 within the housing 302. The sensing circuit 322 senses intrinsic activity, while the change storage unit 324 stores high or low energy amounts to be delivered in one or more stimulus pulses. The electrodes 310-312 may be used to deliver lower energy or high energy stimulus, such as pacing pulses, cardioverter pulse trains, defibrillation shocks and the like. The electrodes 310-312 may also be used to sense electrical activity, such as physiologic and pathologic behavior and events and provide sensed signals to the sensing circuit 322. The electrodes 310-312 are configured to be joined to an energy source, such as a charge storage unit 324. The electrodes 310-312 receive stimulus pulse(s) from the charge storage unit 324. The electrodes 310-312 may be the same or different size. The electrodes 310-312 are configured to deliver high or low energy stimulus pulses to the myocardium.

The LIMD 300 includes a controller 320, within the housing 302 to cause the charge storage unit 324 to deliver activation pulses through each of the electrodes 310-312 in a synchronous manner, based on information from the sensing circuit 322, such that activation pulses delivered from the inner electrode 312 are timed to initiate activation in the adjacent chamber. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The inner and outer electrodes 310-312 are spaced radially and longitudinally apart from one another such that the local activation site (e.g., right atrium) and the distal activation side in the adjacent chamber (e.g., right ventricle) are sufficiently remote from one another within the heart's conductive network to initiate activation in different branches of the hearts conductive network in a time relation that corresponds to the normal hemodynamic timers (e.g., AV delay).

Additionally or alternatively, the LIMD 300 includes a sensor to collect CA signals indicative of at least one of impedance, electrical or mechanical activity by one or more heart chambers or by a local region within the heart. Additionally or alternatively, the CA signals include at least one of EGM signals or heart sound (HS) based CA signals, wherein the HS based CA signals are indicative of one or more of the S1, S2, S3 or S4 heart sounds.

The LIMDs 300 and 301 may communicate with one another to manage atrial pacing in connection with PACs in accordance with embodiments herein. For example, one or both of the LIMDs 300 and 301 may include memory configured to store program instructions and an atrial pace-on-PAC (APAC). One or both of the LIMDs 300 and 301 may include a sensing channel configured to sense cardiac activity (CA) signals, and one or more processors that, when executing the program instructions in a dual chamber mode, are configured to: i) during a first cardiac beat; following a ventricular paced (VP) or ventricular sensed (VS) event, activate a timer for a post ventricular-atrial refractory period (PVARP) interval; and determine whether a first atrial refractory (AR) event occurs during the PVARP interval; and ii) during a second cardiac beat; in response to the detecting that the first AR event occurred, initiate an APAC interval; during the APAC interval for the second cardiac beat, determine whether a second AR event occurs; and update a count of APAC events when the second AR event occurs; and iii) repeat i) and ii) for multiple cardiac beats, to track the count of APAC events.

As a further example, the LIMD 300 in the RA may detect and transmit (via conductive communication or via RF) AS, AR and AP events the LIMD 301 in the RV. The LIMD 301 may then perform the timer activations, determinations and counter updates (of FIG. 5). Alternatively, the LIMD 301 in the RV may detect and transmit (via conductive communication or via RF) VS and VP events the LIMD 300 in the RA. The LIMD 300 may then perform the timer activations, determinations and counter updates (of FIG. 5).

Embodiments may be implemented in connection with one or more subcutaneous implantable medical devices (S-IMDs). Non-limiting examples of S-IMDs include one or more of subcutaneous implantable cardioverter defibrillators (S-ICD). For example, the S-IMD may include one or more structural and/or functional aspects of the device(s) described in U.S. application Ser. No. 15/973,219, titled "IMPLANTABLE MEDICAL SYSTEMS AND METHODS INCLUDING PULSE GENERATORS AND LEADS", filed May 7, 2018; U.S. application Ser. No. 15/973,195, titled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The system includes a subcutaneous implantable medical device (S-IMD) that is configured to be implanted in a subcutaneous area exterior to the heart. The S-IMD is positioned in a subcutaneous area or region, and more particularly in a mid-axillary position along a portion of the rib cage. Optionally, the system may also include a leadless pacemaker implanted within the heart, such as at an apex of the right ventricle. Optionally, the leadless pacemaker may be omitted entirely. The system does not require insertion of a transvenous lead.

The pulse generator may be implanted subcutaneously and at least a portion of the lead may be implanted subcutaneously. In particular embodiments, the S-IMD is an entirely or fully subcutaneous S-IMD. Optionally, the S-IMD may be positioned in a different subcutaneous region.

The S-IMD includes a pulse generator and at least one lead that is operably coupled to the pulse generator. The lead includes at least one electrode segment that is used for providing MV shocks for defibrillation. Optionally, the lead may include one or more sensing electrodes. The pulse generator includes a housing that forms or constitutes an electrode utilized to deliver MV shocks. The electrode associated with the housing of the pulse generator is referred to as the "CAN" electrode.

In an alternative embodiment, the lead may include one or more electrode segments, in which the electrode segments are spaced apart from one another having an electrical gap therebetween. The lead body may extend between the gap. One electrode segment may be positioned along an anterior of the chest, while another electrode segment may be positioned along a lateral and/or posterior region of the patient. The electrode segments may be portions of the same lead, or the electrode segments may be portions of different leads. The electrode segments may be positioned subcutaneously at a level that aligns with the heart of the patient for providing a sufficient amount of energy for defibrillation. The lead includes a lead body that extends from the mid-auxiliary position along an inter-costal area between ribs and oriented with the coil electrode(s) extending along the sternum (e.g., over the sternum or parasternal within one to three centimeters from the sternum). A proximal end the coil electrodes may be located proximate to the xiphoid process.

Next, embodiments herein are described in connection with a process for resolving competitive atrial pacing on a beat by beat basis in accordance with embodiments herein.

Figure 6:
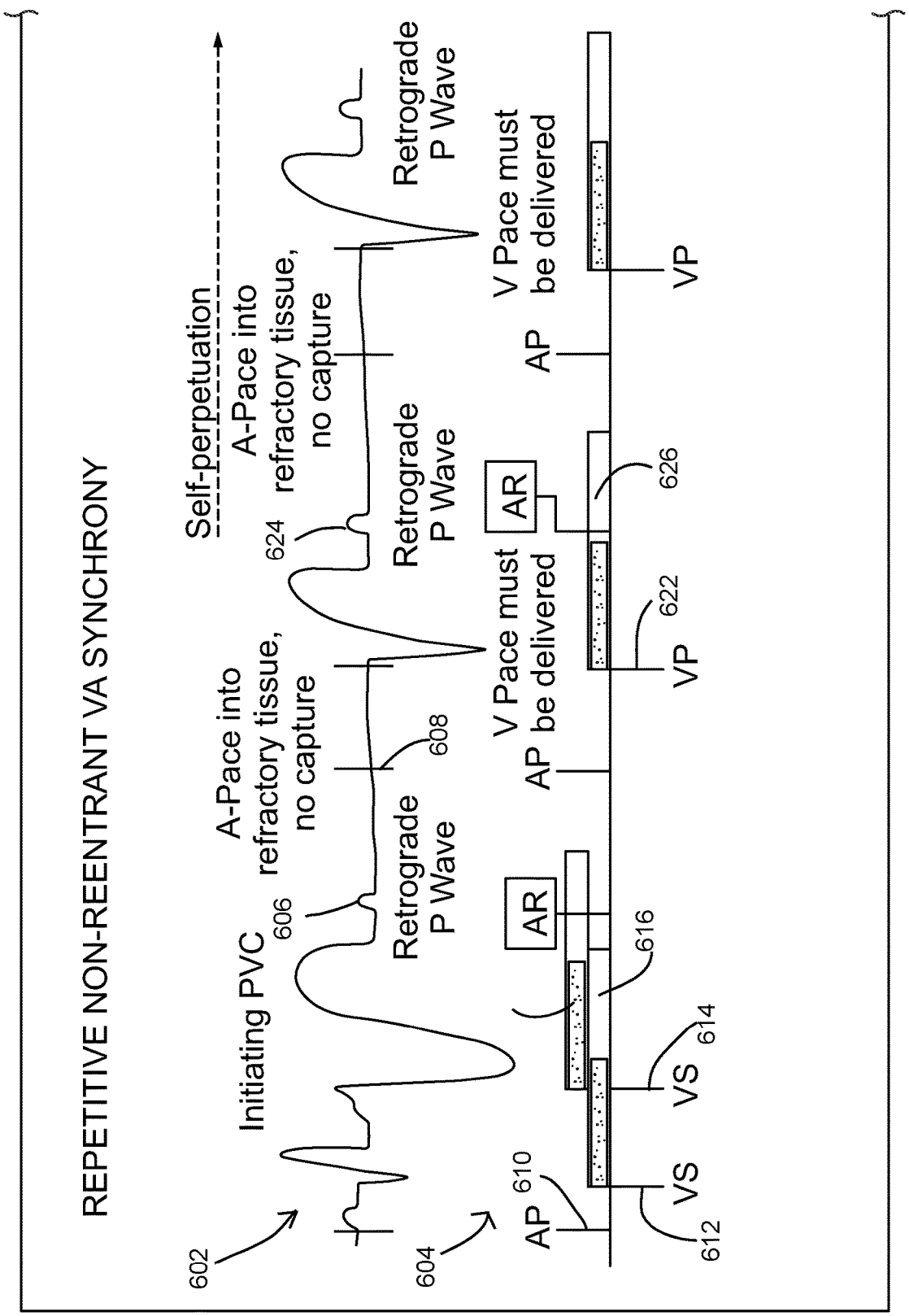
FIG. 6 illustrates CA signals and a marker channel over time, during which the CA signals exhibit repetitive non-reentrant VA synchrony.

FIG. 6 illustrates CA signals 602 and a marker channel 604 over time, during which the CA signals exhibit repetitive non-reentrant VA synchrony. As noted in the CA signals, an initiating premature ventricular contraction (PVC) occurs followed by a retrograde P-wave 606 (also referred to as a premature atrial contraction or PAC). The retrograde P-wave, while falling within the PVARP interval, extends the time period during which the tissue is refractory. Thereafter, an atrial paced event 608 is delivered at a time when the tissue is still refractory, due to the retrograde P-wave, and capture does not occur. As noted in the marker channel, an AP event 610 is initially delivered, followed by detection of two VS events 612, 614. Each VS event is followed by corresponding refractory intervals 616, 618. When in an atrial refractory period 618, the retrograde P-wave/PAC 608 is not detected, and thus when the AR refractory period times out, a next AP event 620 is delivered (while the tissue is refractory). Given that the 2nd AP event 620 does not capture, the device next delivers a VP event 622 (as designated at "VP"). Thereafter, a retrograde P-wave 624 again occurs during the atrial refractory (AR) period 626, and the process becomes a self-perpetuating.

The PVC results in the retrograde P-wave which falls into the PVARP interval. The atrial pacing impulse is delivered into the refractory tissue and given that the AP does not capture, no AV conduction occurs. Hence, the ventricular pacing pulse must be delivered which is followed by another retrograde P-wave within the PVARP interval and the cycle continues. Atrial events may occur during the PVARP interval in several manners. For example, patients may experience retrograde conduction (e.g., a premature atrial contraction), a device may be programmed with a long AV delay, the device may utilize a ventricular intrinsic preference feature or a synchronization AV feature which extend the AV delay as part of a periodic search process. As another example, a rate responsive feature may be disabled.

In accordance with new and unique aspects herein, embodiments provides an "atrial pace on PAC" (APAC) feature that is configured to ensure a minimum interval between an atrial refractory (AR) event and a subsequent atrial paced event. The APAC feature maintains A-V synchrony in the presence of premature atrial contractions and in the presence of atrial events otherwise occurring during the refractory period. The APAC feature reduces the likelihood of induced atrial arrhythmias due to non-physiologic pacing and prevents inappropriate mode switches due to competitive atrial pacing or repetitive non-reentrant VA synchrony. The APAC feature may be enabled as a nominal setting available in certain dual chamber modes, such as DDD and/or DDDR modes with a nominal APAC interval of 330 ms. By way of example, the interval can be programmed between 200-400 ms with a resolution of 10 ms.

Figure 5:
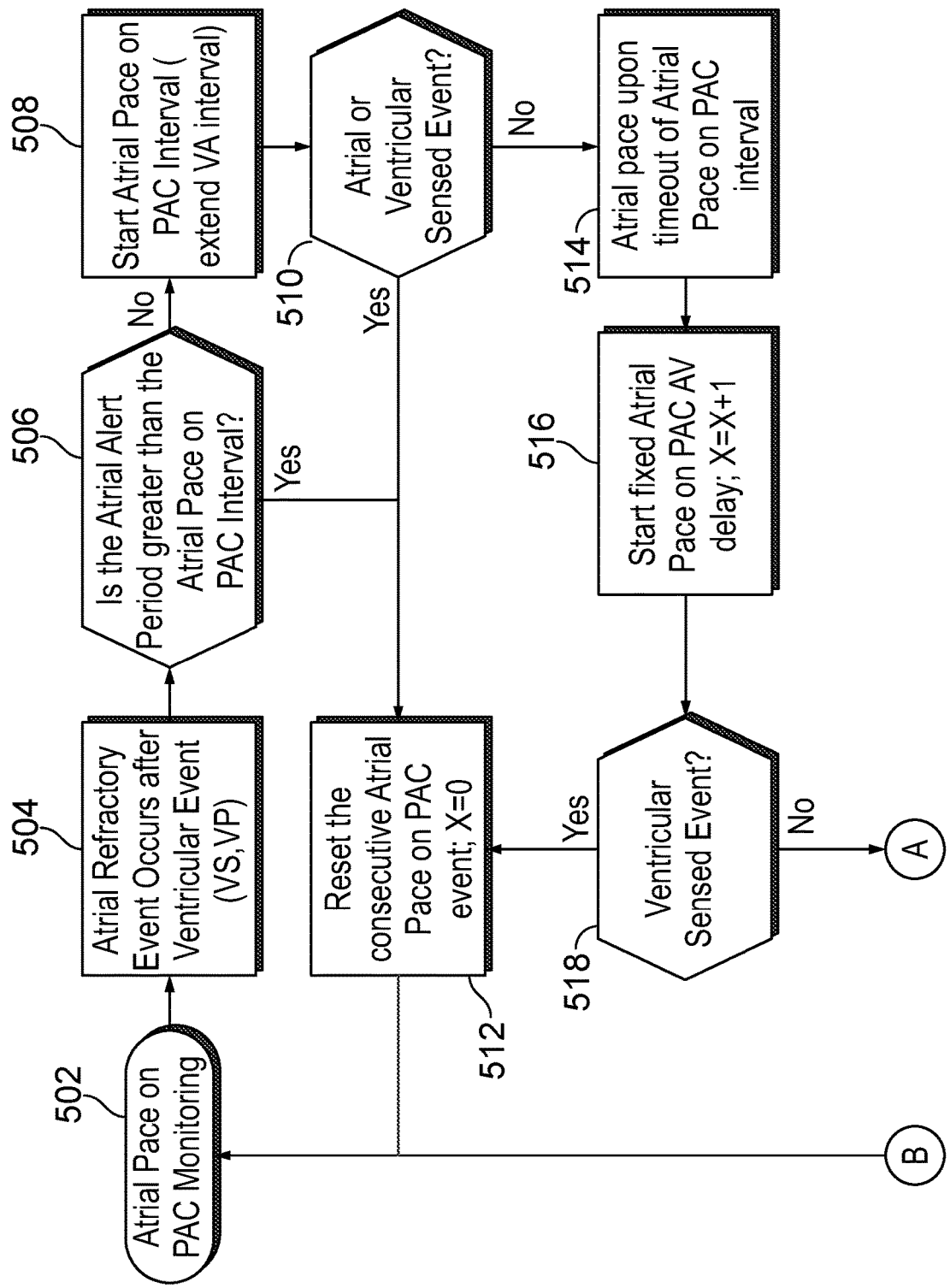
FIG. 5 illustrates a process that monitors for atrial events during the atrial refractory period and manages the APAC interval in accordance with embodiments herein.
Figure 5:
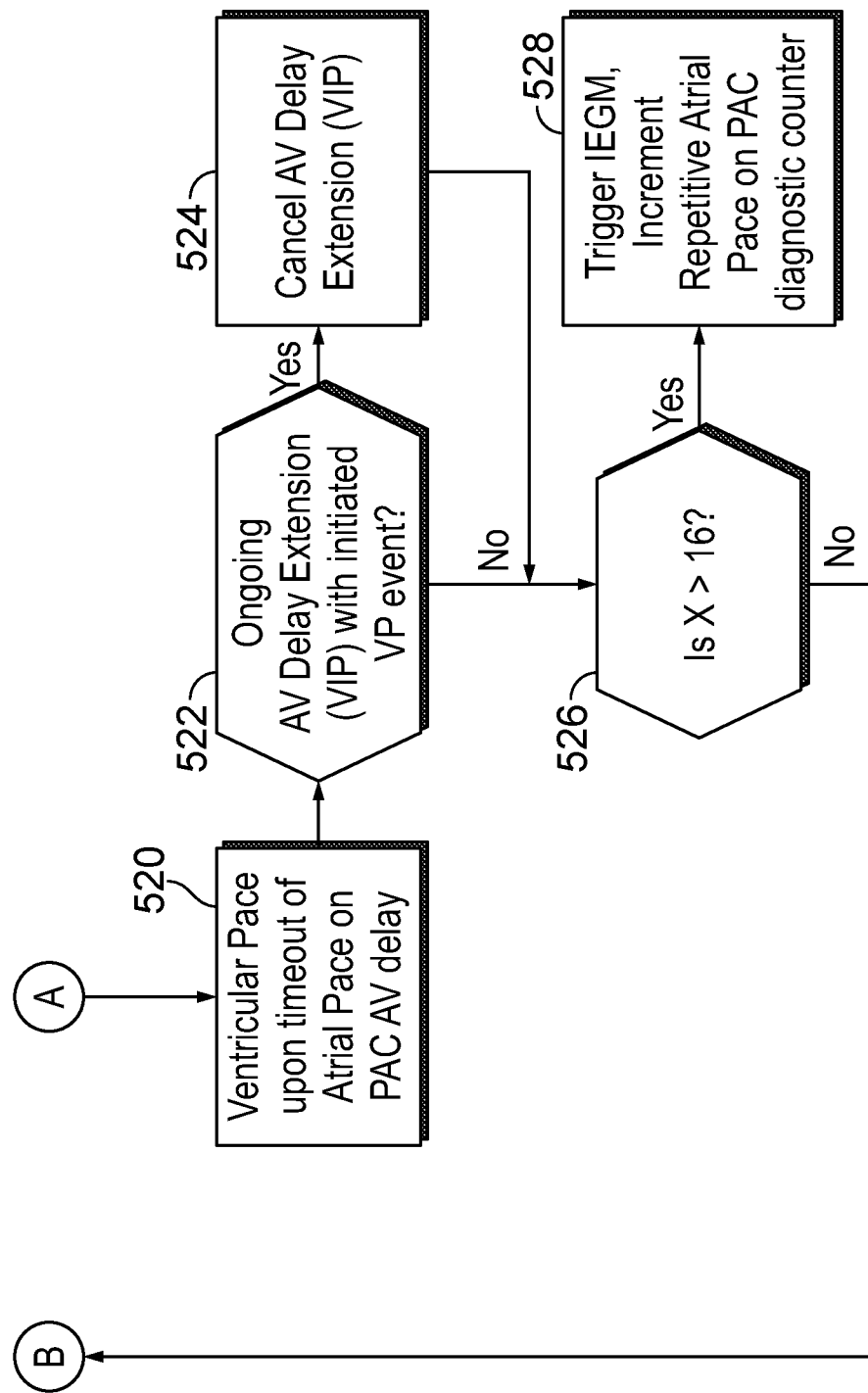

The process of FIG. 5 monitors for atrial events falling in the atrial refractory period, referred to as the post ventricular atrial refractory period (PVARP). Upon detecting an atrial event during the PVARP interval, the process triggers APAC detection. In the absence of other feature interactions, the process resets the timing associated with the next atrial pace to ensure that the minimum time until the next atrial paced (AP) event is equal to the APAC interval. If the interval from the atrial refractory event to the normally scheduled atrial pace is longer than the APAC interval, atrial pacing will continue as dictated by the mode and rate. This allows for the IMD to delay the atrial paced event only when the timing is affected by the feature.

If the APAC interval extends the A-A interval, resulting in an atrial pace due to the process of FIG. 5, then the APAC AV-Delay value is requested (this may violate MTR when the MTR is programmed between 105 and 120.), the combination of extending the A-A interval and requesting an APAC AV-Delay can be understood as the APAC Response. This APAC AV-Delay is a non-programmable value of 100 ms to help discourage the rates of ventricular under sensing, and ventricular arrhythmia induction due to atrial pacing. When the APAC interval is not used, the IMD continues to pace based on the settings of the IMD without any intervention from the APAC process. This allows for the IMD to minimize the ventricular rate change while maintaining reasonable AV synchrony and minimizing the possibility of ventricular induction by reducing the possibility of pacing during the vulnerable period (in the case of pseudo-pseudo fusion).

The initial atrial refractory event (which will cause the APAC interval to be requested) terminates PVARP and initiates an atrial sense refractory equal to the programmed value. This will allow for more appropriate handling of additional p-waves occurring in between the initial atrial refractory event the scheduled atrial pace as described below. Sensing an atrial sense event in the atrial alert period (e.g., falling outside of A-sense refractory triggered by the initial Atrial refractory event) causes the IMD to cancel the APAC interval and track based on the atrial event in accordance with normal pacing behavior. The requested AV delay is extended to prevent this behavior from violating MTR as without this control there is potential for excessively high pacing rates. An event cannot be sensed within the Atrial Sense Refractory triggered by the initial AR event as this is an absolute refractory period, as such, any atrial event occurring during this period is not detected by the device and thus does not impact any timing or diagnostics.

Detection of a ventricular sense (VS) event following triggering the APAC interval suspends APAC and resets the timing as appropriate for the mode and programmed settings. If the VS event is considered a PVC, the IMD will trigger the appropriate PVC response for mode and programmed parameters. Consecutive retriggering of the interval (AP and VP both triggered due to APAC) increments a counter, each additional counter is checked until a count of 16 (a nonprogrammable value) is reached at which point an APAC Timeout is triggered. Following the Timeout, the IMD will continue to behave the same way, counting additional timeouts as they occur. This counter leading up to a timeout can be reset when the algorithm is interrupted by alert period AS or VS events, PVC's or any other pace delivered due to another algorithm. This counter is to serve as a diagnostic to determine why consecutive triggering of the feature is occurring. The device will keep a count of the number of APAC Timeouts that have occurred since last clearing the device diagnostics. Additionally, a SEGM will be triggered following the 16th consecutive ventricular pace at the APAC AV Delay (if enabled). Both the counter and the SEGM can be used for diagnostics purposes as the timeout occurring can be indicative of such device issues as Far-R oversensing, intermittent noise, and an APAC interval not programmed long enough to prevent competitive atrial pacing. These issues can be confirmed by reviewing the SEGM and may result in programming intervention to prevent future occurrence.

If during a ventricular intrinsic preference (VIP) search, A Pace on PAC is triggered following a ventricular paced (VP) event at the VIP extended AV delay and ventricular pacing following an APAC AV delay occurs that interval, then the search interval is cancelled without completing the full search cycle/interval. If the feature response is triggered during VIP extension and the device ventricular senses prior to the extended AV delay timing out then the VIP extension is postponed for the single APAC interval and VIP extension continues the following interval. If the APAC Response is cancelled by additional sensed events then APAC does not impact VIP. This was decided as if the device is pacing during APAC triggering, the patient may be in a transient block state resulting in ventricular pacing resulting in a retrograde P-wave. Cancelling the rest of the search and allowing it to search again at the programmed interval prevents additional re-occurrences.

With the foregoing overview, the discussion now turns to the operations of the example embodiment of FIG. 5. At 502, an APAC feature is enabled and the device begins monitoring cardiac activity (CA) signals sensed over an atrial sensing channel. For example, the atrial sensing channel may sense electrical CA signals by one or more combinations of subcutaneous electrodes for atrial events following a preceding ventricular event. Additionally or alternatively, the atrial sensing channel may utilize an accelerometer or other mechanical sensor to sense heart sounds indicative of HS CA signals. Additionally or alternatively, the CA signals may correspond to impedance measurements.

When implemented in accordance with one or more leadless IMDs, the atrial sensing channel may obtain electrical, HS or impedance CA signals at a local IMD in the atrium or at a remote IMD in the ventricle. For example, a leadless IMD may be implanted in the RV and utilize an accelerometer or other sensor to listen for heart sounds indicative of RA activity (e.g, S1 at closure of the mitral and tricuspid valves, S3 or S4).

Following the ventricular event, whether it is a ventricular sensed event or a ventricular paced (VP) event, a PVARP interval is obtained, a PVARP timer is activated and the one or more processors monitor the atrial sensing channel for CA signals indicative of an atrial event. At 504, one or more processors of the IMD (or of an external device or remote server) analyze the CA signals during the PVARP interval in search of an intrinsic atrial event which represents an AR event. The AR event may be detected as an electrical signal, a heart sound or an impedance. The AR event may be detected by one or more electrodes, an accelerometer or other sensor located in the RA (when detecting a local AR event) or located in the RV or along the LV (when detecting a remote AR event).

At 506, when an AR event is detected during the PVARP interval, the one or more processors obtain a current atrial alert period. The atrial alert period may be defined in various manners. For example, the atrial alert period may be preprogrammed by a clinician to a fixed interval. As another example, the atrial alert period may be set based on the heart rate, when implemented in a rate responsive IMD. For example, the atrial alert period may be set to a percentage of the intrinsic A-A interval, a percentage of the programmed A-A interval and the like. When a patient exhibits a heart rate of 60 BPM, an IMD in a DDDR mode may determine that the intrinsic A-A interval is approximately 1000 ms. The atrial alert period may be set to 10-30 percent of the intrinsic A-A interval. Additionally or alternatively, an IMD may implement a DDD mode, but not be rate responsive. For example, the AA interval and VV interval may be preprogrammed. The atrial alert period may then be programmed to a fixed amount of time based on the programmed AA interval and/or VV interval in the DDD mode.

The one or more processors further obtain an atrial pace-on-PAC (APAC) interval representing a programmed A-A interval between atrial events. For example, the APAC interval may be programmed to between 300 ms and 400 ms, or more preferably between 300 ms and 330 ms. At 506, the one or more processors determine whether a current atrial alert period is greater than a programmed APAC interval. For example, the programmed APAC interval may be 300 ms, while the atrial alert period may only be 200 ms. When the atrial alert period is greater than the APAC interval, flow moves to 512.

At 512, the one or more processors reset a count of consecutive APAC events to X=0. When flow moves from 506 to 512, the timer for the atrial alert period is started but the APAC interval timer is not started.

At 506, when the atrial alert period is less than or equal to the APAC interval, flow moves to 508. When flow moves from 506 to 512, the process omits the initiating, determining and updating in connection with the second cardiac beat (at 508 to 516). Optionally, the decision at 506 may be omitted entirely and flow may move from 504 directly to 508.

At 508, the one or more processors start an APAC interval timer to extend a VA interval. The APAC interval timer runs concurrently with at least a portion of the PVARP interval, although the PVARP interval will typically time out before the APAC interval timer depending upon how earlier in the PVARP interval the AR event occurs. The APAC interval differs from the PVARP interval in various manners. For example, at least one purpose of setting the APAC interval is to ensure there is a desired (e.g., sufficient) time delay between the sensed atrial refractory event and the next atrial paced event. The duration of the APAC interval should be greater than the right atrium's functional refractory period to ensure that the next atrial paced event captures the atrium. The refractory periods of the right atrium can be measured during an electrophysiology study (or periodically by the IMD)

At 510, the one or more processors determine whether an atrial or ventricular sensed event occurs during the APAC interval. When an atrial or ventricular sensed event occurs during the APAC interval, flow moves to 512. Otherwise, flow moves to 514. At 514, the one or more processors determined that the APAC interval timer has timed out without an AS or VS event being detected, and an atrial pace event is delivered.

At 516, the one or more processors increment the count of consecutive APAC events. The APAC event count tracks the number of cardiac beats during which an atrial paced event is delivered following a time out of the APAC interval.

The operations at 502 to 518 are repeated over multiple cardiac beats to track the count of APAC events. For example, during a first cardiac beat, following a ventricular paced (VP) or ventricular sensed (VS) event, the one or more processors activate a timer for the PVARP interval; and determine whether a first atrial refractory (AR) event occurs during the PVARP interval (see operations at 502-506). Then, during a second cardiac beat, in response to the determination that the first AR event occurred, the one or more processors initiate an APAC interval, during the APAC interval for the second cardiac beat, determine whether a second AR event occurs, and update a count of APAC events when the second AR event occurs (see operations at 508 to 516). The APAC event count is incremented over multiple beats until reaching a threshold at 526.

In accordance with at least some embodiments, the process of FIG. 5 may remove the operations at 520 to 524, and instead transition from 518 to 526, without changing the AV delay based on an APAC AV delay.

Optionally, in accordance with at least some embodiments, the process may change the AV delay based on an APAC AV delay in accordance with the operations at 516 to 524. Accordingly, at 516, the one or more processors may further start a programmed APAC AV delay. The APAC AV delay represents an AV delay to be utilized following an occurrence of an AS or AP event in connection with the APAC interval. For example, in APAC AV delay may be preprogrammed to 100 ms or the like.

If the APAC process extends the AA interval and results in an atrial pace event, it is desirable to use an APAC AV delay value, instead of a normal AV delay. For example, a standard AV delay may be programmed to 250 ms or more. When an APAC interval is utilized to extend the AA interval, and an AP event is subsequently delivered, it may be undesirable to wait an additional 250 ms or longer before delivering a VP event. Instead, a shorter AV delay may be defined for the foregoing scenario, referred to as in APAC AV delay. The choice of the APAC AV delay is a compromise between various considerations. For example, it may be desirable to limit or minimize the ventricular rate change, while maintaining a reasonable AV synchrony and while limiting or minimizing a possibility of induction by reducing a possibility of pacing during a vulnerable period. When the APAC interval is added to delay a scheduled atrial paced event, the typical VV interval following a regular paced AV delay may cause a patient to be symptomatic due to the ventricular rate change. Therefore, it may be desirable to utilize a shortened AV delay for VP events following an AP event resulting from and APAC extension to maintain a stable ventricular rate. However, a limit may exist as to how much the paced AV delay can be shortened following in APAC interval given that the minimal amount of time is needed to allow the atrium to fully contract and eject blood to fill the ventricles.

At 518, the one or more processors determine whether a ventricular sensed event is detected during the fixed APAC AV delay, and if so, flow moves to 512. When the APAC AV delay times out without detection of a VS event, flow moves to 520. At 520, the one or more processors deliver a ventricular paced event when the APAC AV delay times out.

At 522, the one or more processors determine whether to apply an ongoing AV delay extension associated with a ventricular intrinsic preference (VIP) upon delivery of a VP event. For example, when features such as VIP and syncAV are enabled, the AV delay may be extended as part of a search process during which the device searches for an intrinsic event. When utilizing the APAC feature in combination with the VIP and/or syncAV features, the potential exists that the APAC interval may result in unduly extending the "extended" AV delay (already extended due to VIP and/or syncAV). In the foregoing scenario, it may be desirable to discontinue the extension of the AV interval due to the VIP and/or syncAV features.

Accordingly, at 522, when the one or more processors determined that an AV delay extension has been applied (e.g., due to VIP or syncAV), flow moves to 524. At 524, the one or more processors cancel the AV delay extension associated with VIP and/or syncAV.

Alternatively, if no AV delay extension has been applied, flow moves to 526.

At 526, the one or more processors determine whether the count of consecutive APAC events has exceeded a threshold (e.g., greater than 16). If not, flow returns to 502. Otherwise, flow moves to 528. At 528, the one or more processors implement certain APAC related diagnostics, such as storing the CA signals (e.g., a predetermined length of IEGM signals), incrementing a repetitive APAC diagnostic counter and the like. The IEGM signals for the prior count of beats (e.g., 16 prior beats) may be moved from a temporary buffer to a longer term storage for later telemetry to an external device along or in combination with other APAC related diagnostics. Additionally or alternatively, the IEGM signals may include CA signals for multiple cardiac beats following the APAC events. Among other diagnostics, the process of FIG. 5 tracks a count of the number of APAC events that occur successively. For example, when an unduly large number of successive APAC events occur, a clinician may determine that the IMD is misclassifying other events as atrial sensed events that are not atrial sensed events. The clinician may reprogram parameters of the IMD such as the sensitivity threshold, sensitivity profile and the like.

Figure 7:
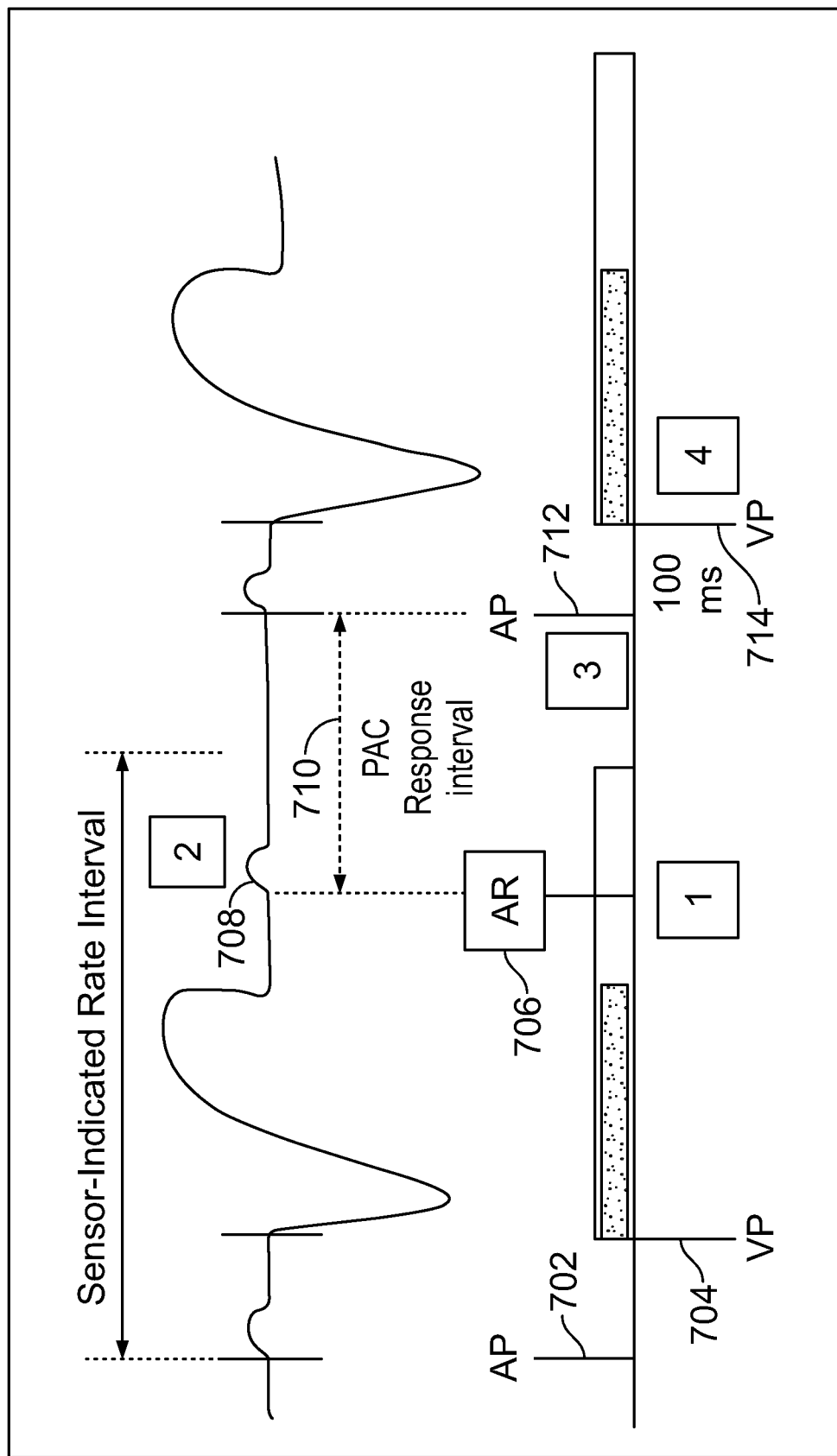
FIG. 7 illustrates example CA signals and corresponding device markers analyzed in connection with the operations of FIG. 5.

FIG. 7 illustrates example CA signals and corresponding device markers analyzed in connection with the operations of FIG. 5. At 702, an AP event is delivered, followed by AV paced event at 704. During the PVARP interval denoted at 706, an A sensed event (also representing an AR event as the AS event occurs during the atrial refractory period) is detected at 708. In response thereto, the APAC response interval is activated 710 which becomes the new atrial alert period for the present cycle and pushes out a scheduled atrial paced event 712. When the APAC interval times out, the atrial paced event is delivered at 712. A fixed paced AV delay is utilized, in connection with which a ventricular paced event is delivered at 714. By way of example, the fixed paced AV delay may be set to a relatively short interval, such as 100 ms.

Figure 8:
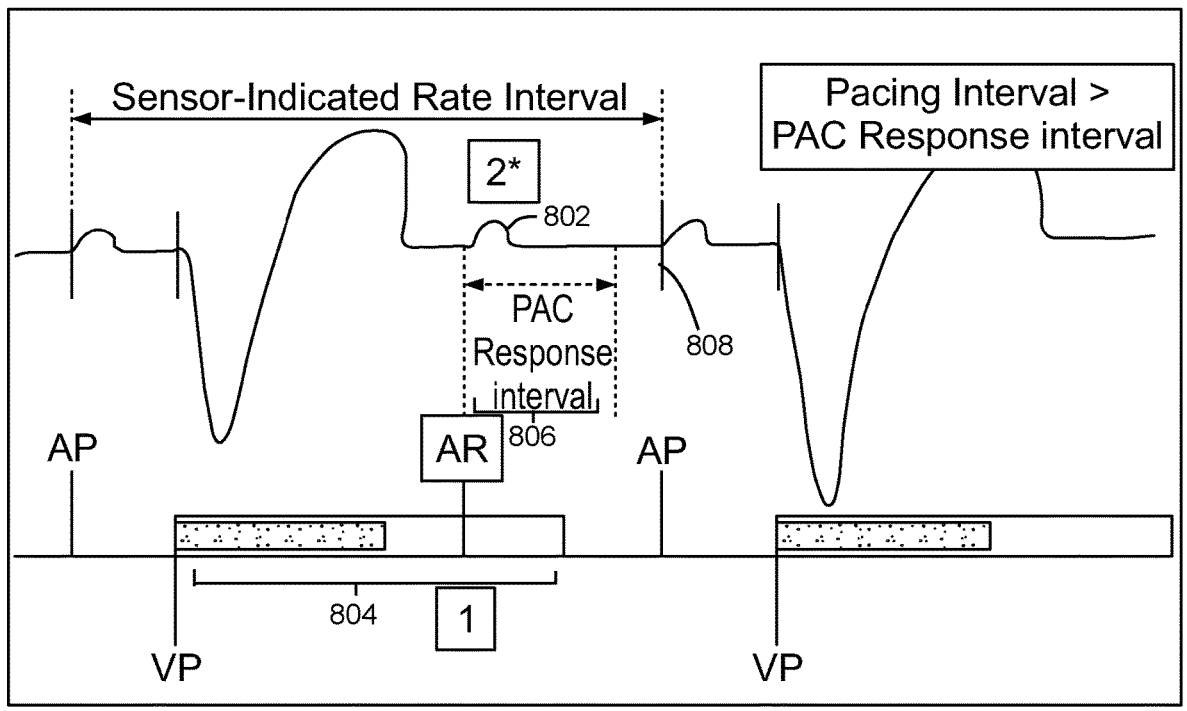
FIG. 8 illustrates an exception that may be utilized in connection with the APAC interval.

FIG. 8 illustrates an exception that may be utilized in connection with the APAC interval. When an intrinsic atrial signal 802 is sensed during the PVARP interval 804, the APAC interval 806 is started. The APAC interval becomes a new atrial alert period for the present cycle and extends the scheduled AP event 808. If no atrial pacing was scheduled to be delivered during the APAC response interval, the device does not apply a pace response, in order to avoid pacing at high rates unnecessarily.

Figure 9:
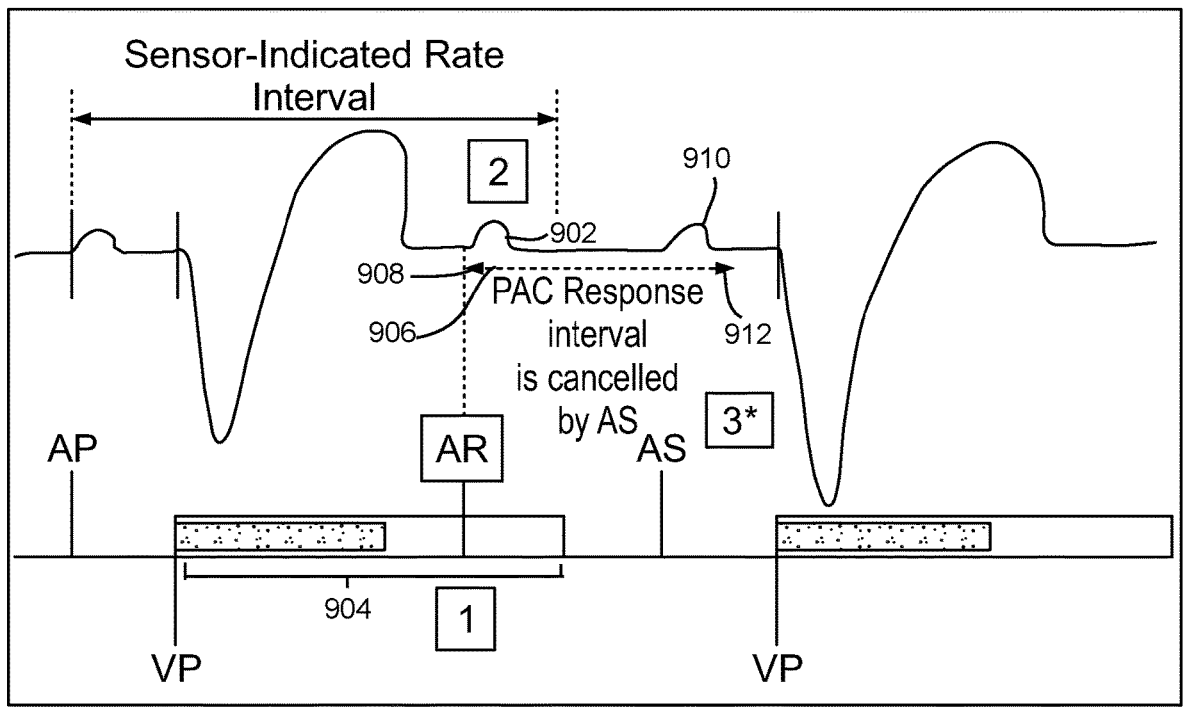
FIG. 9 illustrates an example for when APAC interval may be canceled.

FIG. 9 illustrates an example for when APAC interval may be canceled. Again, an intrinsic atrial signal 902 (also referred to as an AR event) is sensed during the PVARP interval 904). The APAC interval 906 is started at 908, however an intrinsic AS event 910 occurs before the APAC interval times out (at 912) and the APAC interval is canceled and regular programs timing cycles are followed.

Figure 10:
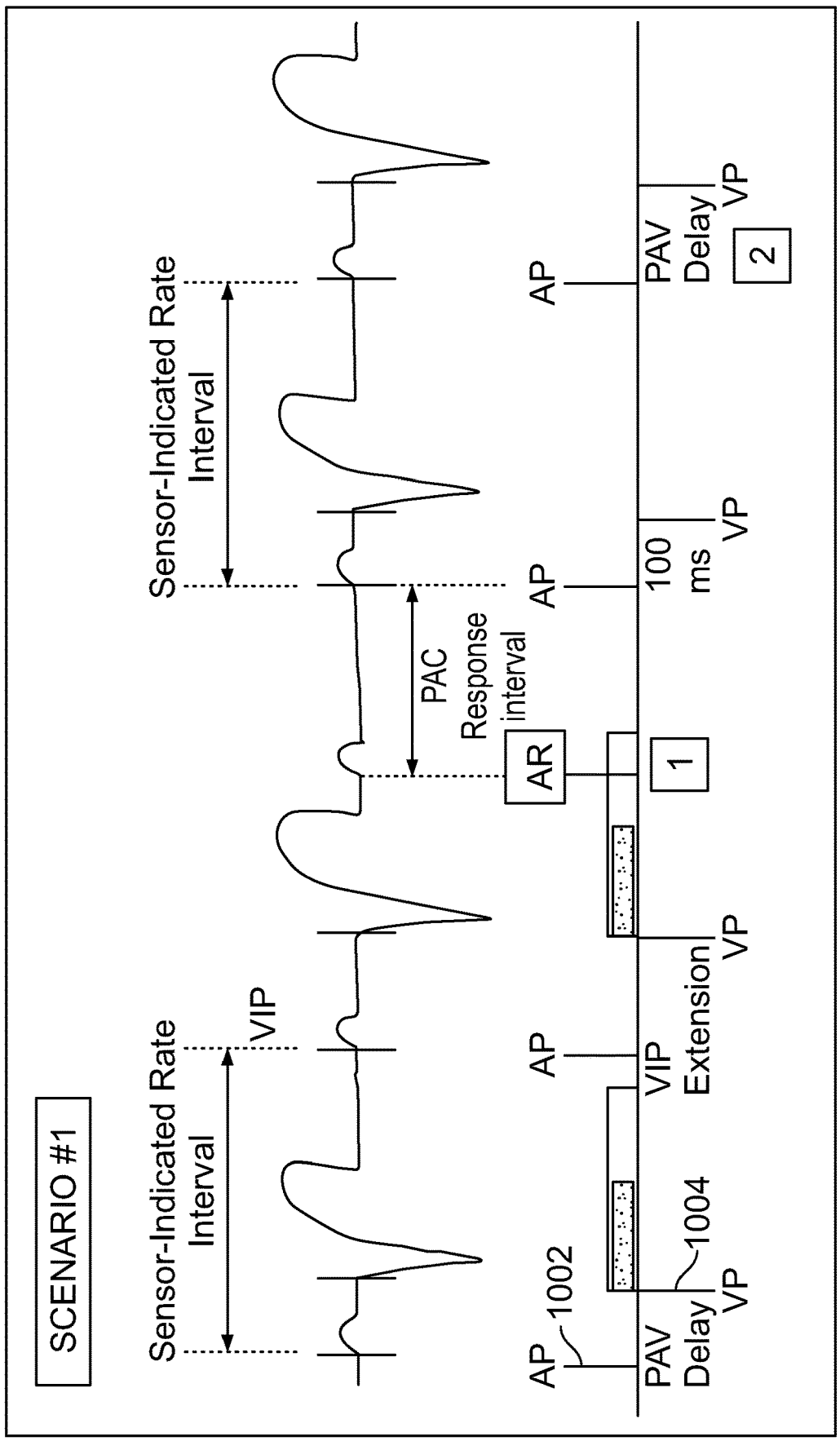
FIG. 10 illustrates an example of the APAC interval interaction during a VIP search.

FIG. 10 illustrates an example of the APAC interval interaction during a VIP search. At 1002, an AP event is delivered, followed by a VP event at 1004 in accordance with the fixed AV delay (e.g., 100 ms later). During the next beat, the VIP search is canceled.

Figure 11:
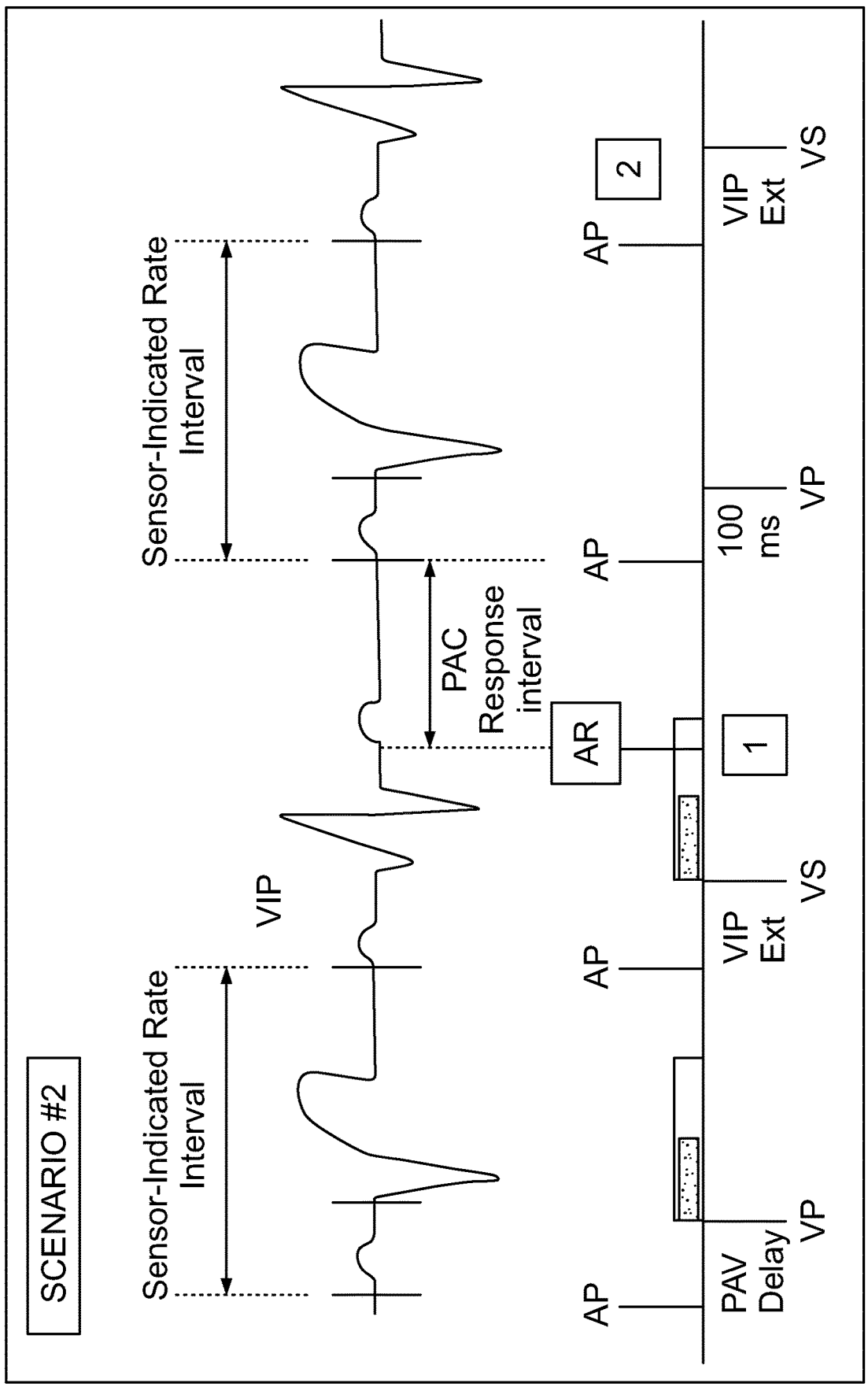
FIG. 11 illustrates another example of the APAC interval interaction during a VIP search.

FIG. 11 illustrates another example of the APAC interval interaction during a VIP search. At 1102, an AP event is delivered, followed by a VP event at 1104 in accordance with the fixed AV delay. During the next beat, the VIP search is resumed.

Figure 12:
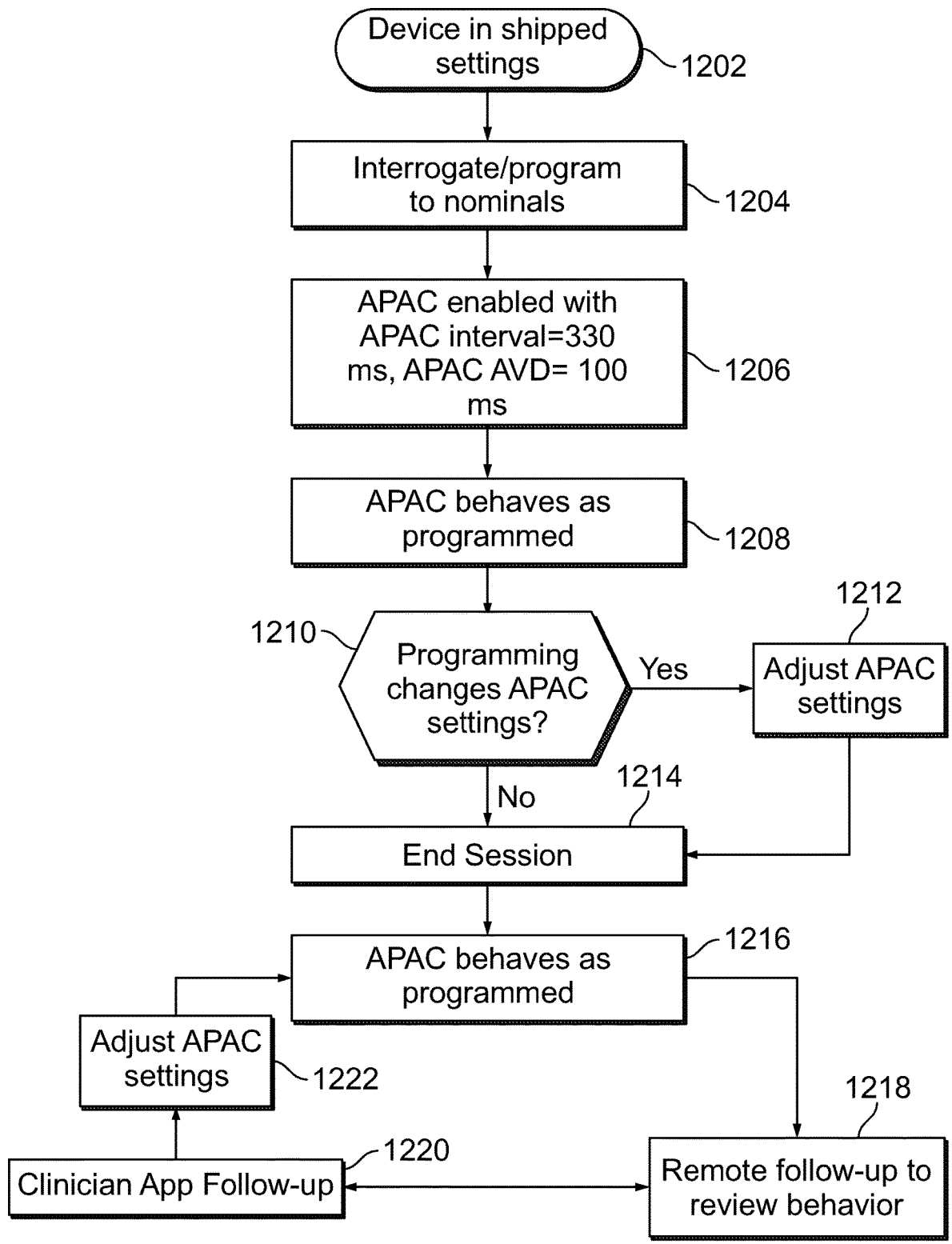
FIG. 12 illustrates a process for managing APAC parameters in accordance with embodiments herein.

FIG. 12 illustrates a process for managing APAC parameters in accordance with embodiments herein. At 1202, an IMD is shipped with factory settings. At 1204, the IMD is interrogated and programmed to nominal settings. Once implanted, at 1206, the APAC feature is enabled with APAC programmed settings/parameters. For example, the APAC interval may be set to 330 ms, while in APAC AV delay may be set to 100 ms. At 1208, the IMD operates in accordance with the program settings for a period of time and various diagnostics and other information recorded. At 1210, a clinician may determine whether the APAC parameters/ settings should be adjusted. If so, flow moves to 1212, where a physician adjust the APAC settings. At 1214, a session between the IMD and an external programmer is ended. At 1216, the IMD operates utilizing the new APAC settings. Thereafter, a remote follow-up may be performed to review the behavior of the device at 1218. Additionally or alterna- tively, a clinician application may communicate with the IMD as a follow-up at 1220, and new APAC settings may be adjusted at 1222.

Additionally or alternatively, a clinical application may be provided that allows for interrogation of the IMD to provide the ability to adjust device parameters and view diagnostic information. This allows the clinician to enable the APAC feature and adjust the settings in connection there with which will also adjust new PVC response intervals. The clinical application also allows a clinician to review and clear diagnostic counters associated with the APAC algorithm timing out.

Additionally or alternatively, a patient application may be provided that operates on a local external device, such as a smart phone, tablet device, laptop computer and the like. The patient application allows for transmission of the feature parameters, diagnostic counters and CA signals associated with the features to a remote server, programmer device or other physician computing device. The patient application may also allow a clinician to remotely clear features associated with diagnostics.

Figure 13:
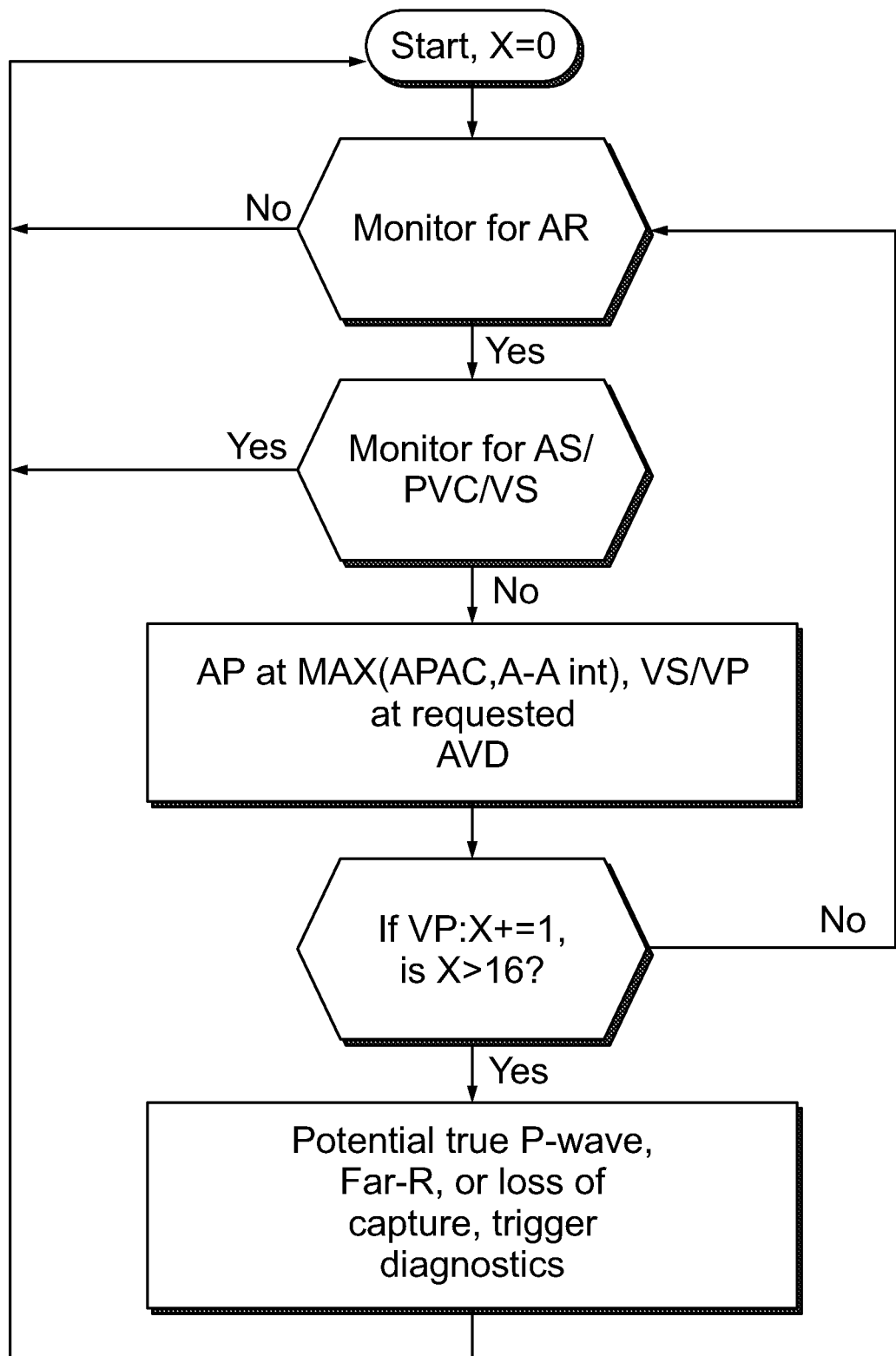
FIG. 13 illustrates a process implemented in accordance with alternative embodiments herein.

FIG. 13 illustrates a process implemented in accordance with alternative embodiments herein. The APAC feature can be enabled or disabled, it is enabled as a nominal setting only available in DDD(R) modes with a nominal APAC interval of 330 ms. This interval can be programmed between 200-400 ms with a resolution of 10 ms. When PVC Response is enabled, programming the APAC Interval or the PVC Response Interval will ensure that the other value is also set as the values are tied together, which is controlled by the Clinician App. To express this behavior, the PVC response interval is redefined in the IMD. Reset with parameter corruption disables APAC as the feature should not be enabled in patients where the clinician had disabled it due to the potential of arrhythmia induction in certain patient populations. APAC is disabled in backup VVI operation due to the nature of the algorithm only being applicable in DDD mode. The feature monitors for atrial events falling into the atrial relative refractory following ventricular events (PVARP) and upon detecting this above a sufficiently high rate, in the absence of other feature interactions, the device resets the next atrial pace to ensure that the minimum time until the next AP is equal to the APAC interval. If the interval from the atrial refractory event to the normally scheduled atrial pace is longer than the APAC interval, APAC is not triggered and atrial pacing will continue as dictated by the mode and rate.

If the APAC interval extends the A-A interval, resulting in an atrial pace due to the algorithm, then the APAC AV-Delay value is requested (this may violate MTR when the MTR is programmed between 105 and 120,) the combination of extending the A-A interval and requesting an APAC AV-Delay can be understood as the APAC Response. This APAC AV-Delay is a non-programmable value of 100 ms to help discourage the rates of ventricular under sensing, and ventricular arrhythmia induction due to atrial pacing. It is a separate value from the Shortest AV Delay (which was originally considered to be used instead of a separate APAC AV-Delay) to prevent the value from getting accidentally programmed to a value that may not be clinically appropriate for this feature. When the APAC interval is not used, the device continues to pace per device settings without any intervention from APAC.

The initial atrial refractory event which will cause the APAC interval to be requested terminates PVARP and initiates an atrial sense refractory equal to the programmed value. This will allow for more appropriate handling of additional p-waves occurring in between the initial atrial refractory event the scheduled atrial pace as described below.

Sensing an atrial sense event in the atrial alert period (falling outside of A-sense refractory triggered by the initial Atrial refractory event) causes the device to cancel the APAC interval and track off that atrial event per normal pacing behavior (the requested AV delay is extended to prevent this behavior from violating MTR as without this control there is potential for excessively high pacing rates). An event cannot be sensed within the Atrial Sense Refractory triggered by the initial AR event as this is an absolute refractory period, as such, any atrial event occurring during this period is not detected by the device and thus does not impact any timing or diagnostics.

Detection of a VS following triggering the APAC interval suspends APAC and resets the timing as appropriate for the mode and programmed settings. If this VS is considered a PVC, the device will trigger the appropriate PVC response for mode and programmed parameters. Consecutive retriggering of the interval (AP and VP both triggered due to APAC) increments a counter, each additional counter is checked until a count of 16 (a non-programmable value) is reached at which point an APAC Timeout is triggered. Following the timeout, the device algorithm will continue to behave the same way, counting additional timeouts as they occur. This counter leading up to a timeout can be reset when the algorithm is interrupted by alert period AS or VS events, PVC's or any other pace delivered due to another algorithm. This counter is to serve as a diagnostic to determine why consecutive triggering of the feature is occurring. The device will keep a count of the number of APAC Timeouts that have occurred since last clearing the device diagnostics. Additionally, a SEGM will be triggered following the 16th consecutive ventricular pace at the APAC AV Delay (if enabled). Both the counter and the SEGM can be used for diagnostics purposes as the timeout occurring can be indicative of such device issues as Far-R oversensing, intermittent noise, and an APAC interval not programmed long enough to prevent competitive atrial pacing. These issues can be confirmed by reviewing the SEGM and may result in programming intervention to prevent future occurrence.

The feature SEGM storage and trigger priority are both lowest preventing these SEGM's from overwriting any other EGM and allowing all other EGM's to overwrite them. Additionally, the most recent APAC Timeout episode is protected as it will provide clinically actionable information and will only contain a 14 second pre-trigger and 2 second post-trigger. The length of such an EGM will not take up a significant amount of device memory. This SEGM trigger is nominally disabled as there is a potential that many of these episodes may cause clinician confusion if too many are stored at a time. Originally it was proposed that the EGM trigger priority would be lowest while the storage priority would be most-recent EGM is protected, and the device would only store a single EGM at a time. It was later determined that the extra code involved in changing EGM storage paradigm would not be worth the benefit so the resulting EGM storage scheme above is a compromise. Additionally, the 14 second pre-trigger and 2-second post-trigger should allow the EGM to contain initiation through triggering of the timeout and will also show a few second past to confirm that the rhythm did not break after the EGM was triggered. These diagnostics will allow the clinician to know important clinical data as described in the preceding paragraph concerning what may have caused the algorithm to consecutively trigger and potentially make programming changes to prevent this in the future.

If during a VIP search, APAC is triggered following a VP at the VIP extended AVD and ventricular pacing following an APAC AV delay occurs that interval, then the search interval is cancelled without completing the full search cycle/interval. If the feature response is triggered during VIP extension and the device ventricular senses prior to the extended AV delay timing out then the VIP extension is postponed for the single APAC interval and VIP extension continues the following interval. If the APAC Response is cancelled by additional sensed events then APAC does not impact VIP.

SyncAV with search will interact with APAC similarly to VIP. During the AV delay extension out to 300 ms if an AR event is sensed following a VP event then the AV/PV extension will be cancelled for that interval. The terminate criteria is different for SyncAV compared to VIP in that SyncAV will only cancel the extension on the current interval and then continue searching following this. This is okay as the main point of SyncAV is to measure and then reduce the occurrence of v-sensing, whereas VIP is meant to reduce the occurrence of V-pacing. Consequently, cancelling the search makes more sense for VIP where pacing is discouraged than in SyncAV where pacing is encouraged. If an AR event is sensed following a VS event then the search will simply be postponed for that single interval and resume its search from there. If the APAC Response is cancelled by additional sensed events then APAC does not impact SyncAV.

Arrhythmia unhiding can request an interval extension, this has resulted in competitive atrial pacing in the field because the AV delay is extended which pushes out the PVARP and this causes sinus P-waves to be covered by PVARP. This would cause the APAC algorithm to detect a PAC and request the APAC interval. In most cases this will be interrupted by an additional VS event or another P-wave, if either interrupt occurs arrhythmia unhiding requested intervals will continue to be used. If the device reaches the end of the APAC interval and paces in the atrium, the APAC AV Delay will be used as the requested AV Delay, it does not need to postpone arrhythmia unhiding for this interval however because arrhythmia unhiding will only extend PV delays per device firmware.

If mode switches occur to modes other than DDD then the APAC algorithm is suspended for the duration of the mode switch. Episodal pacing will suspend the algorithm to minimize any potential impact on SVT discriminators as well as to minimize ventricular pacing during potential ventricular episodes. Episodal pacing suspends the algorithm for the duration that the device is under Episodal pacing parameters.

Episodal pacing will suspend the algorithm while PVEs will not, because ICDs were going to be able to be programmed to a MTR greater than the VT detect rate and in cases where the device is pacing within the VT zones, conducted ventricular events would cancel the algorithm which was not desired behavior from a Clinical Perspective.

The APAC feature has the potential to interact with PVC Response as well. In cases where APAC and PVC Response are both on and a PVC occurs and is followed by an atrial event in PVARP, PVC Response will take precedence over APAC and will respond accordingly. If a PVC occurs during the APAC response, the PVC Response will take over and respond. If PVC response is Off a PVC will be handled as an interrupt to the APAC Response by resetting the pacing interval as dictated by programmed settings.

If PMT response is enabled and is in the middle of detection of a PMT when an atrial event is sensed within PVARP and APAC is triggered, the APAC Response will occur. If PMT has been detected and a PMT episode has been sensed the algorithm will suspend APAC until the PMT Response has concluded at which time APAC will be re-enabled.

The APAC feature is only active in DDD/DDDR mode, reprogramming the mode to any other value will disable the algorithm. Programming the device from other modes to DDD will automatically enable the algorithm with the nominal APAC Interval programmed. Temp programming within a session will automatically suspend the APAC feature for the duration of temp programming. If any change in programming is made to either the APAC Interval or the PVC Response interval, the clinician App will auto program the other interval to ensure they are always programmed the same while the two features are on together.

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. An implantable medical device (IMD) for managing atrial (A) pacing in connection with premature atrial contracts (PAC), comprising:
    memory configured to store program instructions and an atrial pace-on-PAC (APAC) interval;
    a sensing channel configured to sense cardiac activity (CA) signals; and
    one or more processors that, when executing the program instructions in a dual chamber mode, are configured to:
    i) during a first cardiac beat;
        following a ventricular paced (VP) or ventricular sensed (VS) event, activate a timer for a post ventricular-atrial refractory period (PVARP) interval; and
        determine whether a first atrial refractory (AR) event occurs during the PVARP interval;
    ii) during a second cardiac beat;
        in response to the detecting that the first AR event occurred, initiate an APAC interval;
        during the APAC interval for the second cardiac beat, determine whether a second AR event occurs; and
        update a count of APAC events when the second AR event occurs; and
    iii) repeat i) and ii) for multiple cardiac beats, to track the count of APAC events.

2. The IMD of claim 1, wherein the one or more processors are further configured to determine when the count of APAC events exceeds a threshold and in response thereto, transmitting APAC related diagnostics to an external device.

3. The IMD of claim 2, wherein the APAC related diagnostics include IEGM signals for the multiple beats that included the APAC events.

4. The IMD of claim 1, wherein the one or more processors are further configured to obtain an atrial alert period, compare the atrial alert period to the APAC interval and manage the initiation of the APAC interval based on the comparing.

5. The IMD of claim 4, wherein, when the atrial alert period is less than or equal to the APAC interval, the one or more processors are further configured to perform the initiate, determine and update operations in connection with the second cardiac beat.

6. The IMD of claim 4, wherein, when the atrial alert period is greater than the APAC interval, the one or more processors are further configured to reset the count of the APAC events and omit the initiate, determine and update operations in connection with the second cardiac beat.

7. The IMD of claim 1, further comprising a transmitter configured to communicate with a second IMD to obtain the CA signals, perform the i) and ii) operations and track the count the APAC events.

8. The IMD of claim 1, wherein the APAC interval has a duration set to achieve a desired time delay between the AR event and a next atrial paced event, the duration of the APAC interval greater than a right atrium functional refractory period such that the next atrial paced event captures the atrium.

9. The IMD of claim 1, wherein the one or more processors are further configured to start a programmed APAC AV delay that represents an AV delay to be utilized following an occurrence of an AS or AP event in connection with the APAC interval.

10. The IMD of claim 9, wherein the APAC AV delay is configured to limit or minimize a ventricular rate change, while maintaining a desired AV synchrony and while limiting or minimizing a possibility of induction by reducing a possibility of pacing during a vulnerable period.

11. The IMD of claim 9, wherein the one or more processors are further configured to discontinue an extension of an AV interval when the APAC AV delay is started.

12. A method for managing atrial (A) pacing in connection with premature atrial contracts (PAC), comprising:
    obtaining an atrial pace-on-PAC (APAC) interval;
    obtaining cardiac activity (CA) signals;
    under control of one or more processors within one or more implantable medical device (IMD) operating in a dual chamber mode,
    ii) during a first cardiac beat;
        following a ventricular paced (VP) or ventricular sensed (VS) event, activating a timer for a post ventricular-atrial refractory period (PVARP) interval; and
        determining whether a first atrial refractory (AR) event occurs during the PVARP interval;
    ii) during a second cardiac beat;
        in response to the detecting that the first AR event occurred, initiating an APAC interval;
        during the APAC interval for the second cardiac beat, determining whether a second AR event occurs; and
        updating a count of APAC events when the second AR event occurs; and
    iii) repeating i) and ii) for multiple cardiac beats, to track the count of APAC events.

13. The method of claim 12, further determining when the count of APAC events exceeds a threshold and in response thereto, transmitting APAC related diagnostics to an external device.

14. The method of claim 13, wherein the APAC related diagnostics include IEGM signals for the multiple beats that included the APAC events.

15. The method of claim 12, further comprising obtaining an atrial alert period, comparing the atrial alert period to the APAC interval and managing the initiating of the APAC interval based on the comparing.

16. The method of claim 15, wherein, when the atrial alert period is less than or equal to the APAC interval, performing the initiating, determining and updating in connection with the second cardiac beat.

17. The method of claim 15, wherein, when the atrial alert period is greater than the APAC interval, resetting the count of the APAC events and omitting the initiating, determining and updating in connection with the second cardiac beat.

18. The method of claim 12, wherein the APAC interval has a duration set to achieve a desired time delay between the AR event and a next atrial paced event, the duration of the APAC interval greater than a right atrium functional refractory period such that the next atrial paced event captures the atrium.

19. The method of claim 12, wherein the APAC interval runs concurrently with at least a portion of the PVARP interval, and the PVARP interval will time out before the APAC interval.

20. The method of claim 12, wherein the CA signals represent at least one of electrical CA signals, heart sound CA signals or impedance CA signals.

* * * * *